(12) United States Patent
Baroud

(10) Patent No.: US 9,867,646 B2
(45) Date of Patent: Jan. 16, 2018

(54) INTEGRATED CEMENT DELIVERY SYSTEM FOR BONE AUGMENTATION PROCEDURES AND METHODS

(71) Applicant: Gamal Baroud, Sherbrooke (CA)

(72) Inventor: Gamal Baroud, Sherbrooke (CA)

(*) Notice: Subject to any disclaimer, the term of this patent is extended or adjusted under 35 U.S.C. 154(b) by 9 days.

(21) Appl. No.: 14/956,866

(22) Filed: Dec. 2, 2015

(65) Prior Publication Data

US 2016/0081732 A1    Mar. 24, 2016

Related U.S. Application Data

(63) Continuation-in-part of application No. 13/790,378, filed on Mar. 8, 2013, now Pat. No. 9,204,913, which
(Continued)

(51) Int. Cl.
 *A61B 17/88* (2006.01)
 *A61B 10/02* (2006.01)
(Continued)

(52) U.S. Cl.
 CPC .... *A61B 17/8805* (2013.01); *A61B 5/150015* (2013.01); *A61B 5/150099* (2013.01);
(Continued)

(58) Field of Classification Search
 CPC ............ A61B 17/8819; A61B 17/8822; A61B 17/8816; A61B 17/8805
 See application file for complete search history.

(56) References Cited

U.S. PATENT DOCUMENTS 1,988,480 A    1/1935   Campkin
2,602,446 A    7/1952   Glass et al.
(Continued)

FOREIGN PATENT DOCUMENTS

CA    2434151    7/2002
CA    2524140    12/2003
(Continued)

OTHER PUBLICATIONS

International Search Report PCT/CA2007/00579; dated Jul. 25, 2007.
European Search Report EP 07 71 9509; dated Jun. 1, 2010.

*Primary Examiner* — Christian Sevilla
(74) *Attorney, Agent, or Firm* — Norton Rose Fulbright Canada

(57) ABSTRACT

A method of harvesting bone marrow, including percutaneously introducing a multi-lumen cannula into a cancellous bone, applying suction through a first passage defined in a first lumen of the cannula, injecting a thick flowable material into the bone from a second passage in a second lumen of the cannula, extruding the thick flowable material through a distal end of the cannula into the cancellous bone in order to displace the bone marrow and other bone fluids, the suction applied through the first passage providing a hydraulic force guiding the displaced bone marrow and collecting the displaced bone marrow for a therapeutic or diagnostic purpose. A thick flowable material for use in harvesting bone marrow in the cancellous portion of a bone and a method for percutaneously preparing a bone with a multi-lumen cannula and an inflatable device are also discussed.

14 Claims, 22 Drawing Sheets

Related U.S. Application Data is a continuation of application No. 12/246,798, filed on Oct. 7, 2008, now Pat. No. 8,409,211, which is a continuation-in-part of application No. PCT/CA2007/000579, filed on Apr. 5, 2007.

(60) Provisional application No. 60/789,891, filed on Apr. 7, 2006.

(51) Int. Cl.

| | | |
|---|---|---|
| *A61L 24/08* | (2006.01) | |
| *A61B 18/06* | (2006.01) | |
| *A61N 5/10* | (2006.01) | |
| *A61B 5/15* | (2006.01) | |
| *A61M 5/142* | (2006.01) | |
| *A61M 5/145* | (2006.01) | |
| *A61B 5/03* | (2006.01) | |
| *A61M 5/20* | (2006.01) | |
| *A61M 5/32* | (2006.01) | |
| *A61M 5/34* | (2006.01) | |
| *A61M 5/48* | (2006.01) | |
| *A61B 17/00* | (2006.01) | |
| *A61B 90/00* | (2016.01) | |
| *A61B 18/00* | (2006.01) | |
| *A61B 90/50* | (2016.01) | |
| *A61B 34/10* | (2016.01) | |

(52) U.S. Cl.
CPC .. *A61B 5/150213* (2013.01); *A61B 5/150389* (2013.01); *A61B 5/150503* (2013.01); *A61B 10/025* (2013.01); *A61B 17/8811* (2013.01); *A61B 17/8816* (2013.01); *A61B 17/8819* (2013.01); *A61B 17/8822* (2013.01); *A61B 18/06* (2013.01); *A61L 24/08* (2013.01); *A61M 5/142* (2013.01); *A61M 5/1456* (2013.01); *A61M 5/14566* (2013.01); *A61N 5/1007* (2013.01); *A61B 5/03* (2013.01); *A61B 34/10* (2016.02); *A61B 90/37* (2016.02); *A61B 90/50* (2016.02); *A61B 2010/0258* (2013.01); *A61B 2017/00685* (2013.01); *A61B 2017/8844* (2013.01); *A61B 2018/00565* (2013.01); *A61B 2018/00577* (2013.01); *A61B 2090/032* (2016.02); *A61B 2090/064* (2016.02); *A61B 2090/3916* (2016.02); *A61B 2090/3966* (2016.02); *A61B 2218/002* (2013.01); *A61B 2218/007* (2013.01); *A61F 2230/0069* (2013.01); *A61F 2230/0071* (2013.01); *A61M 5/20* (2013.01); *A61M 5/32* (2013.01); *A61M 5/329* (2013.01); *A61M 5/3286* (2013.01); *A61M 5/347* (2013.01); *A61M 5/484* (2013.01); *A61M 5/488* (2013.01); *A61N 2005/1021* (2013.01)

(56) References Cited

U.S. PATENT DOCUMENTS

| | | |
|---|---|---|
| 2,627,270 A | 2/1953 | Glass |
| 2,690,178 A | 9/1954 | Bickford |
| 2,702,547 A | 2/1955 | Glass |
| 3,365,936 A | 1/1968 | Hubin et al. |
| 3,623,474 A | 11/1971 | Hellman et al. |
| 3,631,847 A | 1/1972 | Hobbs, II |
| 3,701,345 A | 10/1972 | Hellman et al. |
| 4,099,528 A | 7/1978 | Sorenson et al. |
| 4,180,068 A | 12/1979 | Jacobson et al. |
| 4,202,332 A | 5/1980 | Tersteegen et al. |
| 4,236,109 A | 11/1980 | Ingle, Jr. |
| 4,294,251 A | 10/1981 | Greenwald et al. |
| 4,399,100 A | 8/1983 | Zsolnay et al. |
| 4,423,371 A | 12/1983 | Senturia et al. |
| 4,884,573 A | 12/1989 | Wijay et al. |
| 4,891,591 A | 1/1990 | Johnston et al. |
| 4,952,205 A | 8/1990 | Mauerer et al. |
| 5,007,904 A | 4/1991 | Densmore et al. |
| 5,012,818 A | 5/1991 | Joishy |
| 5,092,453 A | 3/1992 | Bruke |
| 5,108,404 A | 4/1992 | Scholten et al. |
| 5,145,250 A | 9/1992 | Planck et al. |
| 5,211,477 A | 5/1993 | Li |
| 5,279,149 A | 1/1994 | Williams et al. |
| 5,436,565 A | 7/1995 | Gammell |
| 5,681,286 A | 10/1997 | Niehoff |
| 5,681,317 A | 10/1997 | Caldarise |
| 5,685,821 A | 11/1997 | Pike |
| 5,718,678 A | 2/1998 | Fleming, III |
| 5,800,439 A | 9/1998 | Clyburn |
| 5,872,447 A | 2/1999 | Hager, III |
| 5,898,309 A | 4/1999 | Becker et al. |
| 5,947,929 A | 9/1999 | Trull |
| 6,066,154 A | 5/2000 | Reiley et al. |
| 6,179,569 B1 | 1/2001 | Kojima et al. |
| 6,241,734 B1 | 6/2001 | Scribner et al. |
| 6,348,055 B1 | 2/2002 | Preissman |
| 6,368,307 B1 | 4/2002 | Ziemba et al. |
| 6,575,936 B1 | 6/2003 | Kojima et al. |
| 6,613,054 B2 | 9/2003 | Scribner et al. |
| 6,958,053 B1 | 10/2005 | Reilly |
| 6,979,352 B2 | 12/2005 | Reynolds |
| 7,008,433 B2 | 3/2006 | Voellmicke et al. |
| 7,112,205 B2 | 9/2006 | Carrison |
| 7,153,307 B2 | 12/2006 | Scribner et al. |
| 7,226,481 B2 | 6/2007 | Kuslich |
| 7,465,290 B2 | 12/2008 | Reilly |
| 7,549,977 B2 | 6/2009 | Schriver et al. |
| 7,563,249 B2 | 7/2009 | Schriver et al. |
| 7,572,263 B2 | 8/2009 | Preissman |
| 7,662,133 B2 | 2/2010 | Scarberough et al. |
| 8,409,211 B2 | 4/2013 | Baroud |
| 2001/0049531 A1 | 12/2001 | Reiley et al. |
| 2002/0058947 A1 | 5/2002 | Hochschuler et al. |
| 2002/0173796 A1 | 11/2002 | Cragg |
| 2004/0191897 A1* | 9/2004 | Muschler ........... A61B 10/0233 435/325 |
| 2004/0225292 A1 | 11/2004 | Sasso et al. |
| 2004/0260303 A1 | 12/2004 | Carrison |
| 2005/0070915 A1 | 3/2005 | Mazzuca et al. |
| 2005/0113843 A1 | 5/2005 | Arramon |
| 2005/0131390 A1 | 6/2005 | Heinrich et al. |
| 2005/0177111 A1 | 8/2005 | Ozeri et al. |
| 2005/0234498 A1 | 10/2005 | Gronemeyer et al. |
| 2006/0074433 A1 | 4/2006 | McGill et al. |
| 2006/0079905 A1 | 4/2006 | Beyar et al. |
| 2006/0089655 A1 | 4/2006 | Watkins et al. |
| 2006/0122621 A1 | 6/2006 | Truckai et al. |
| 2006/0122624 A1 | 6/2006 | Truckai et al. |
| 2006/0149379 A1 | 7/2006 | Kuslich et al. |
| 2007/0027230 A1 | 2/2007 | Beyar et al. |
| 2007/0032567 A1 | 2/2007 | Beyar et al. |
| 2007/0118144 A1 | 5/2007 | Truckai et al. |
| 2007/0191858 A1 | 8/2007 | Truckai et al. |
| 2007/0198024 A1 | 8/2007 | Plishka et al. |
| 2008/0065089 A1 | 3/2008 | Osorio et al. |
| 2008/0119821 A1 | 5/2008 | Agnihotri et al. |
| 2008/0195114 A1 | 8/2008 | Murphy |
| 2008/0249530 A1 | 10/2008 | Truckai et al. |
| 2010/0286616 A1 | 11/2010 | Baroud |

FOREIGN PATENT DOCUMENTS

| | | |
|---|---|---|
| CA | 2545436 | 5/2005 |
| CA | 2575699 | 2/2006 |
| CA | 2603010 | 10/2006 |
| DE | 10008481 | 9/2001 |
| DE | 102004043294 | 3/2006 |
| FR | 2819714 | 7/2002 |

(56) References Cited

FOREIGN PATENT DOCUMENTS

| | | |
|---|---|---|
| WO | 02/000143 | 1/2002 |
| WO | 02100282 | 12/2002 |
| WO | 2006/062939 | 6/2006 |

* cited by examiner

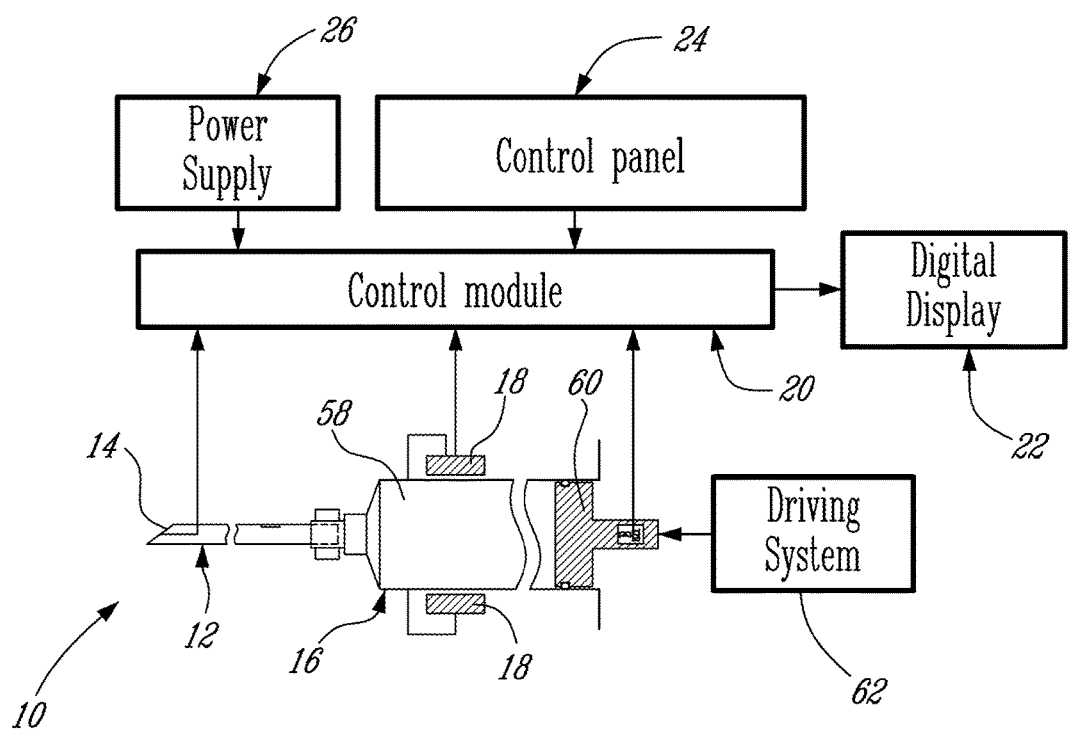
FIG_1

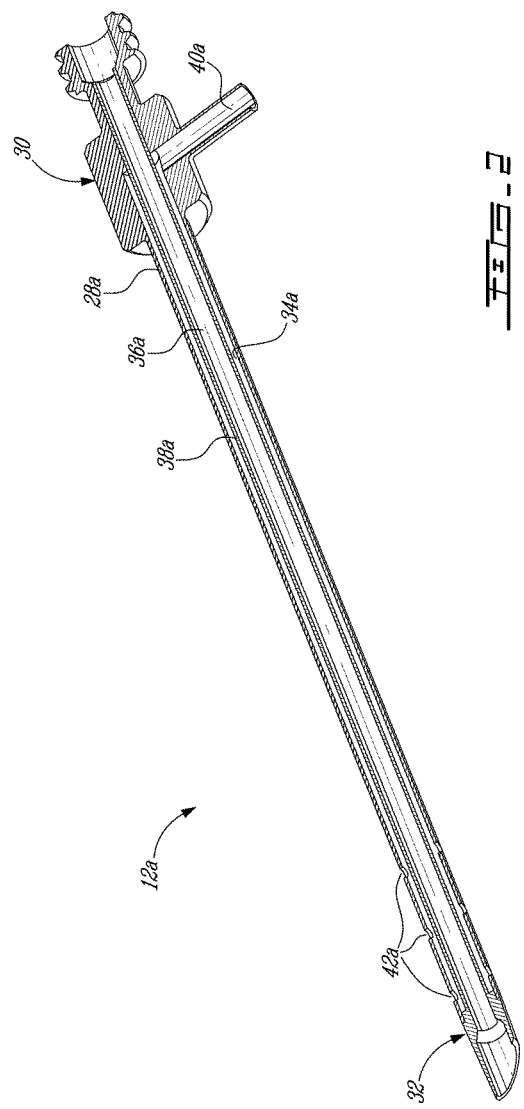

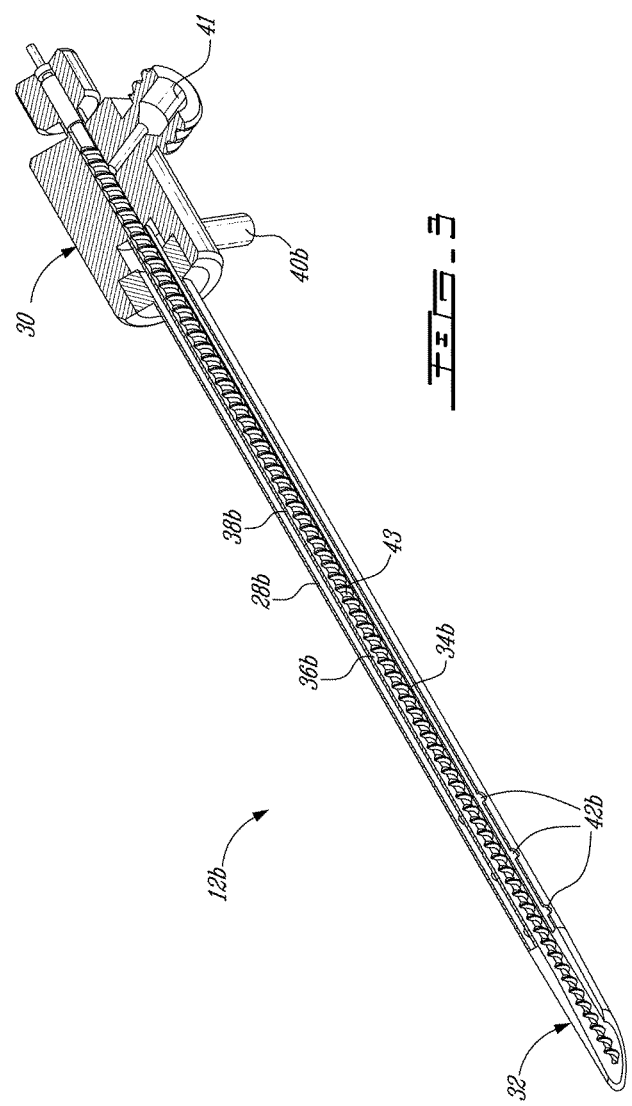

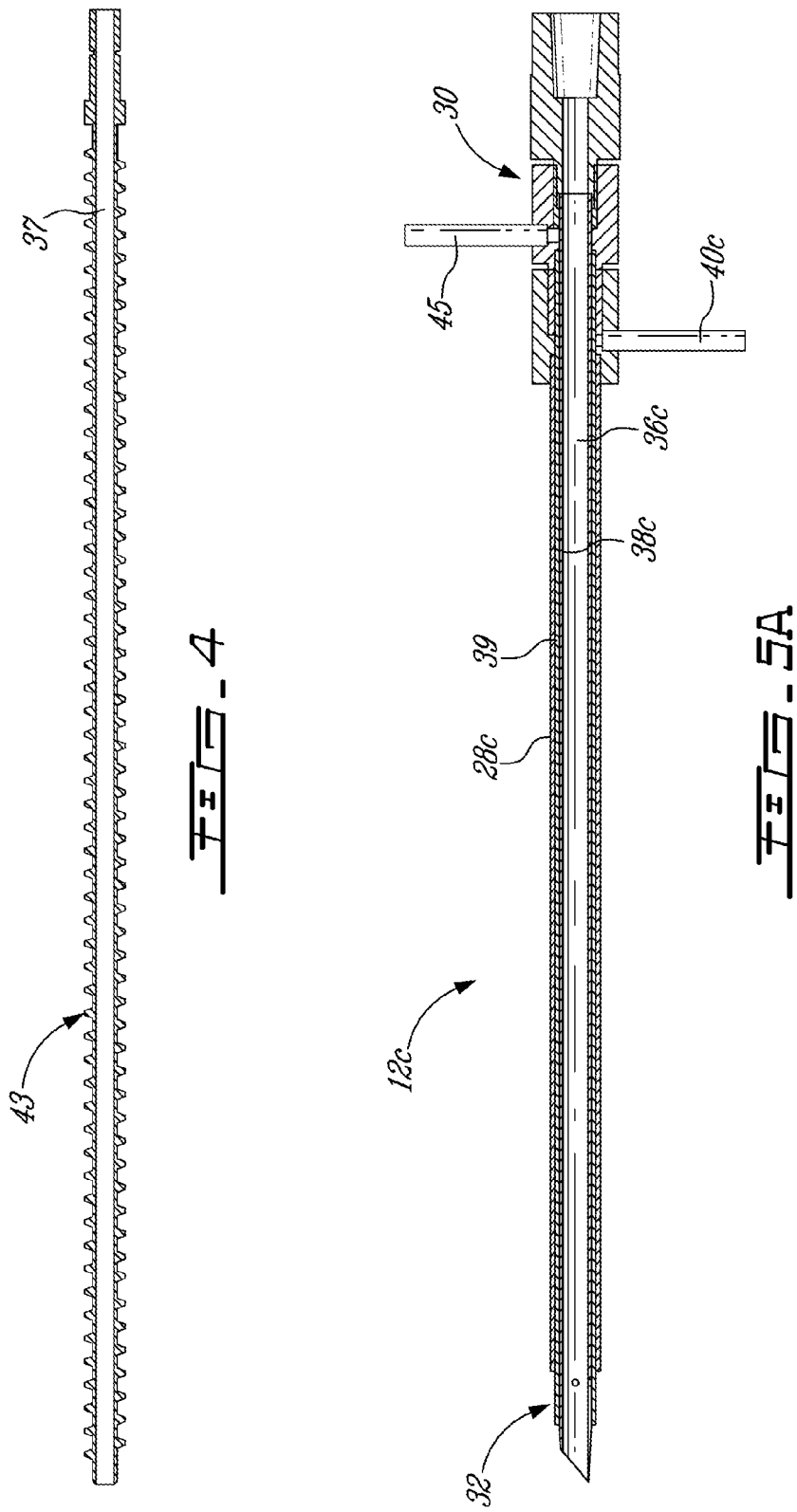

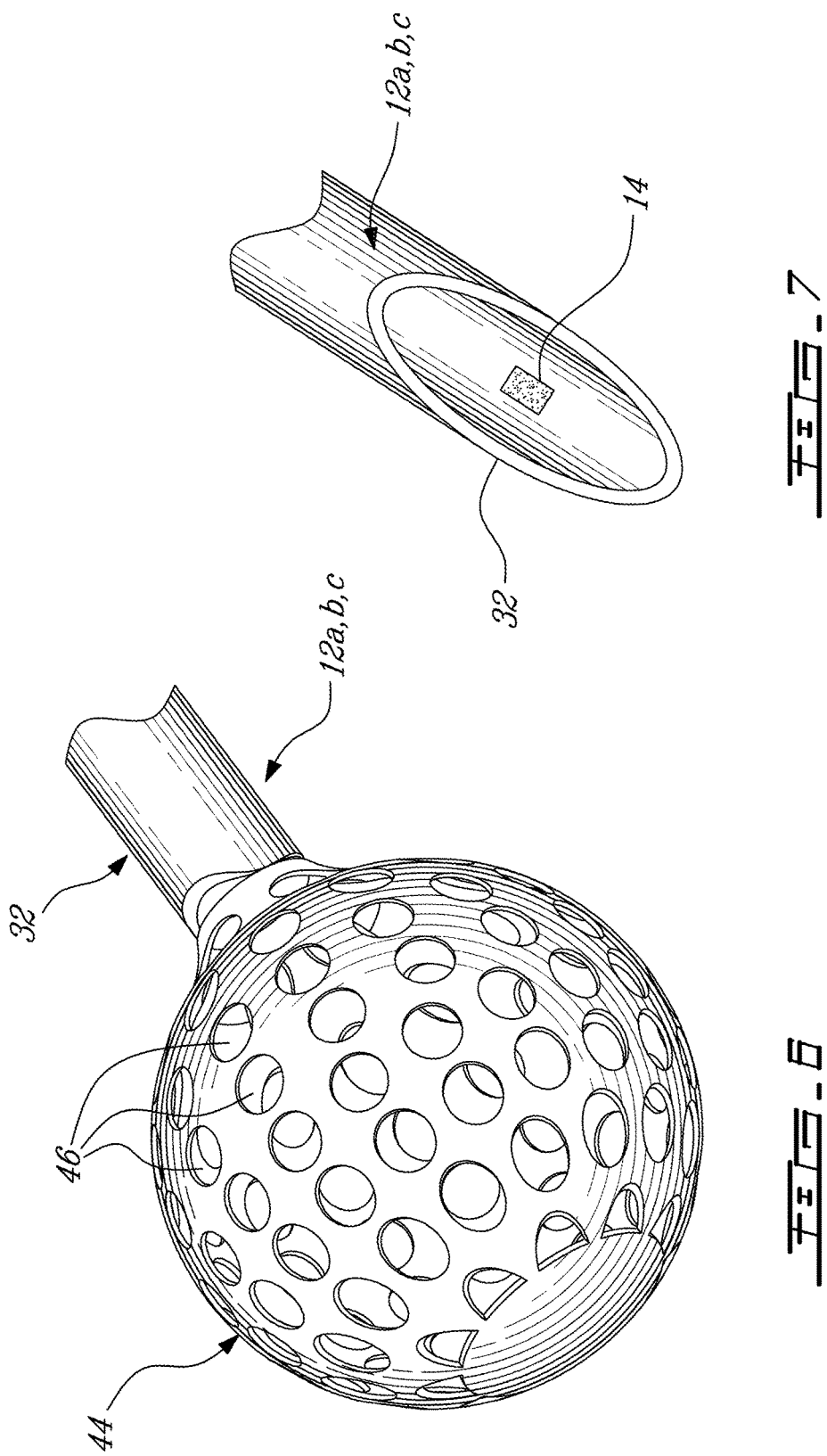

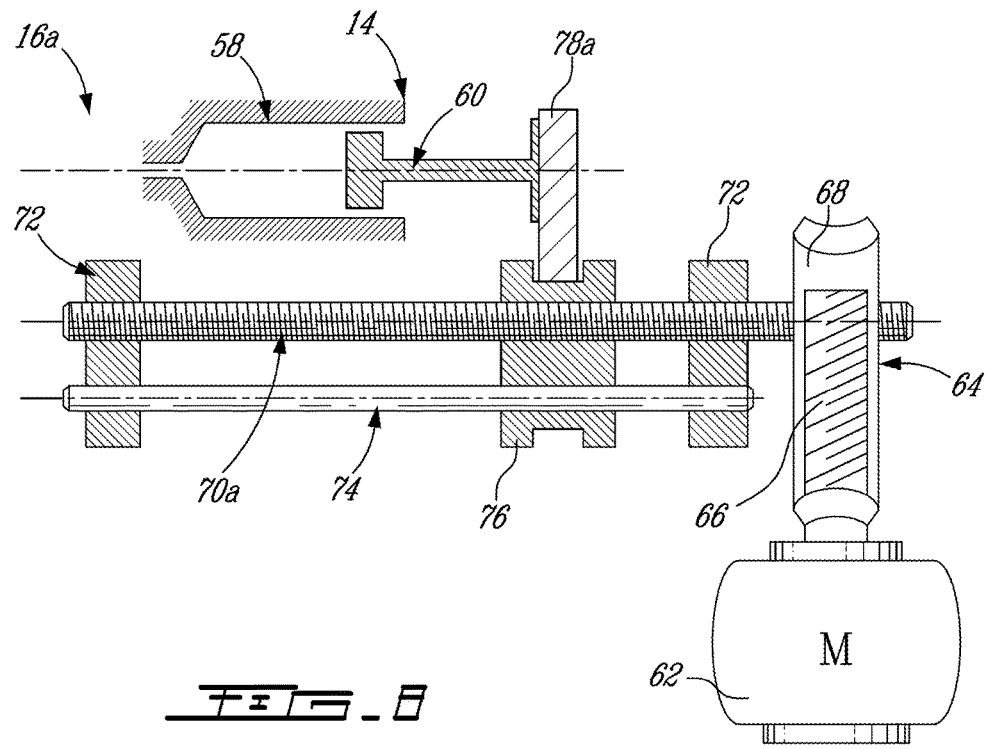
FIG_8
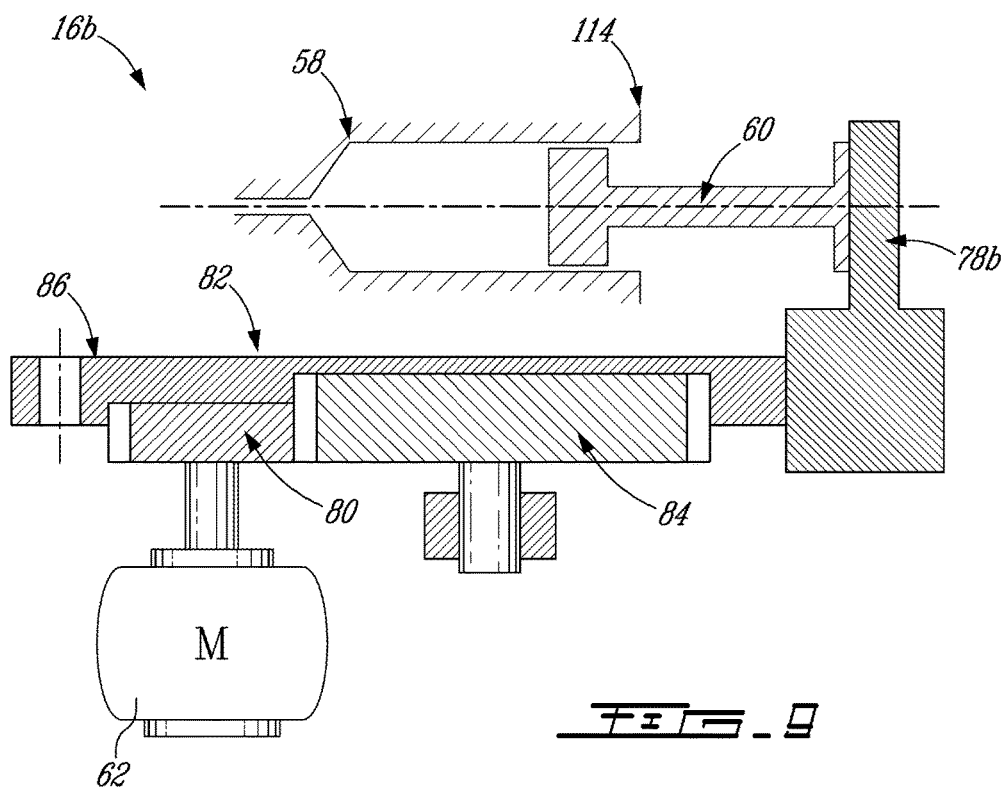
FIG_9

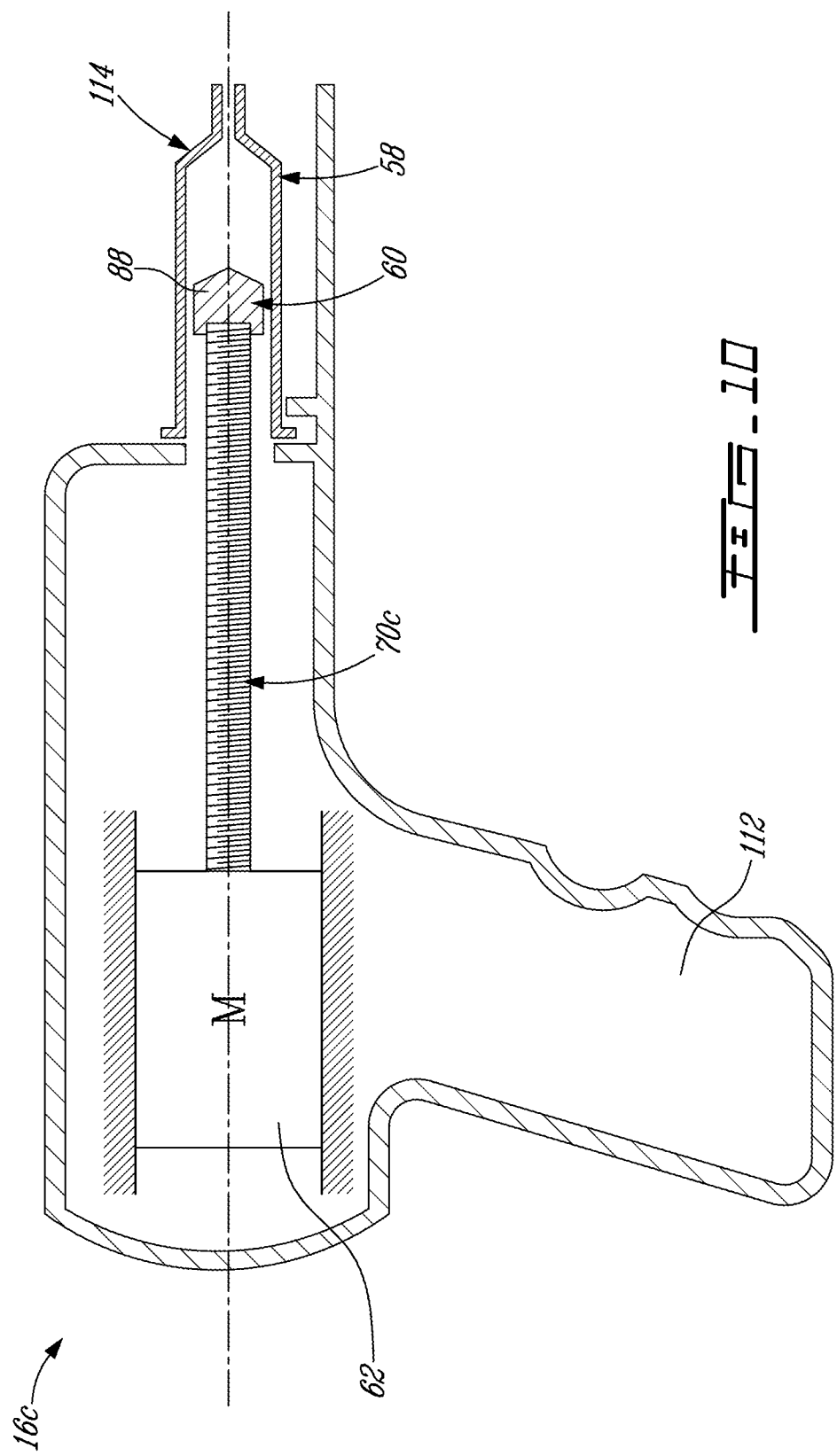

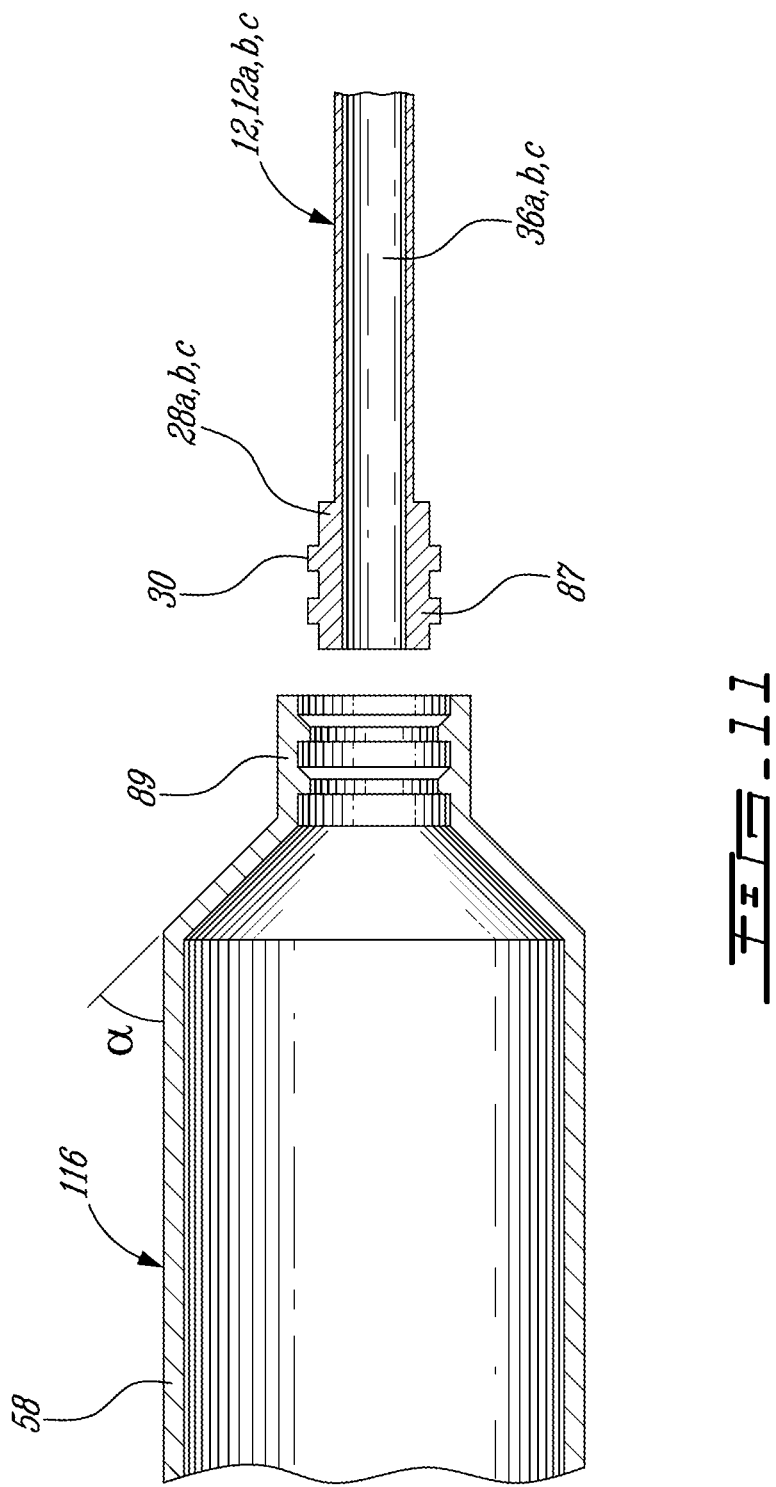

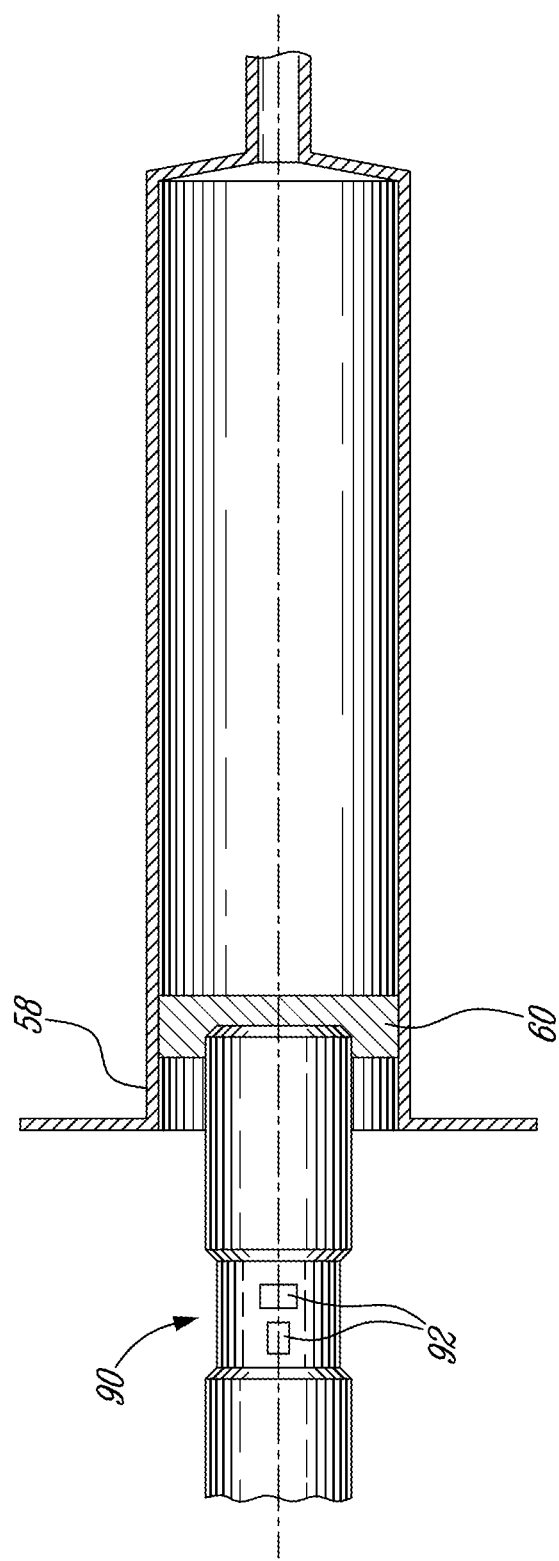

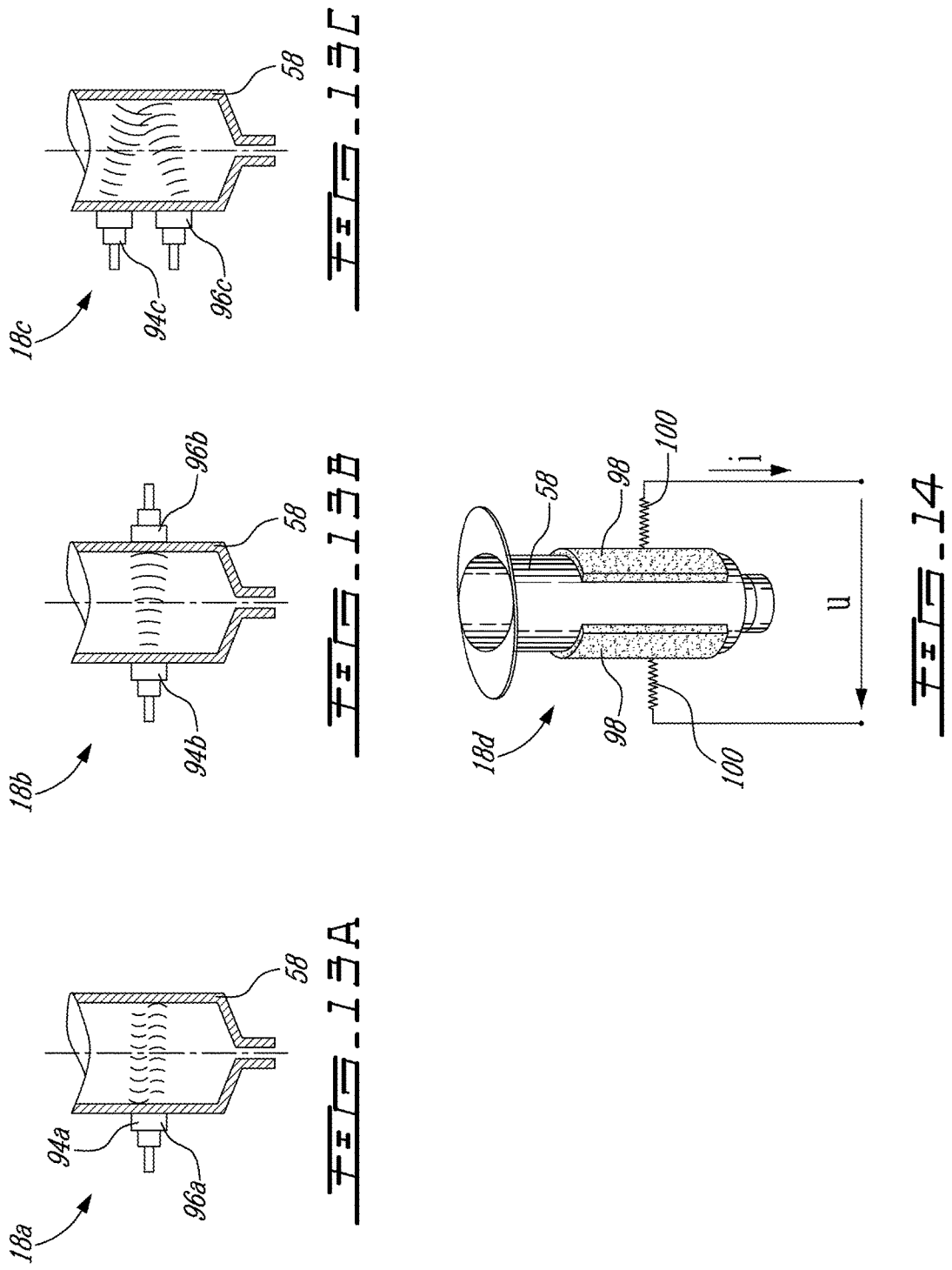

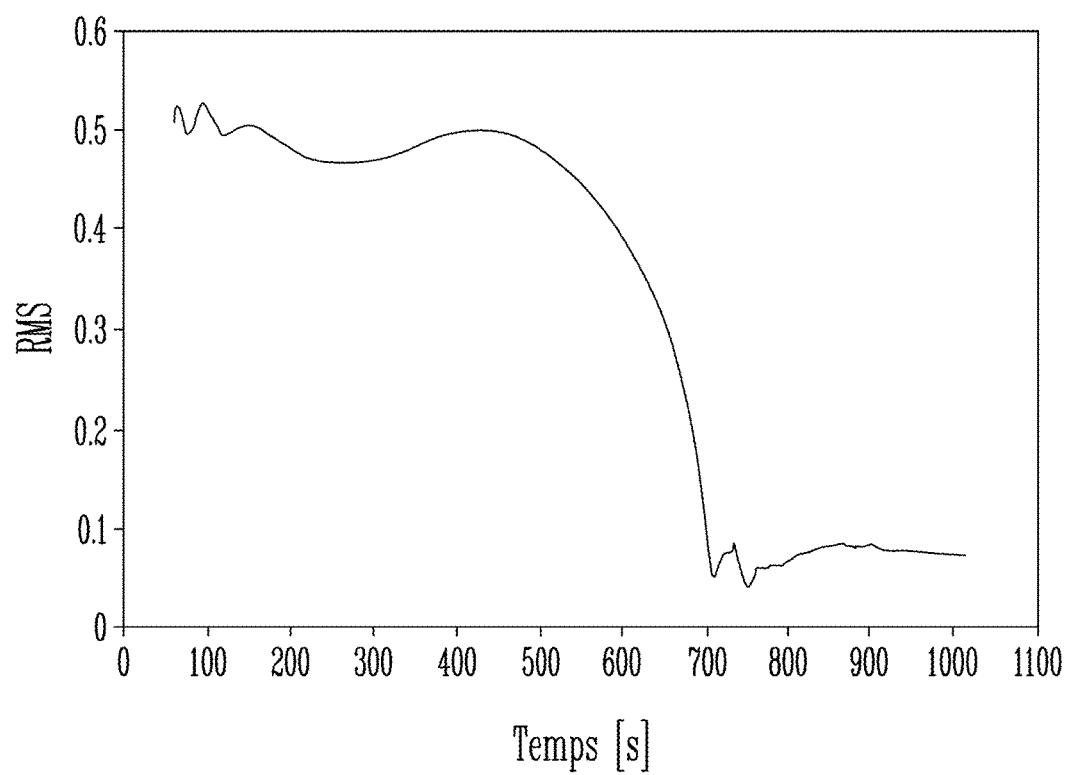
FIG_16

FIG_23

INTEGRATED CEMENT DELIVERY SYSTEM FOR BONE AUGMENTATION PROCEDURES AND METHODS

CROSS-REFERENCE TO RELATED APPLICATIONS

This application is a continuation-in-part of U.S. application Ser. No. 13/790,378 filed Mar. 8, 2013, which is a continuation of U.S. application Ser. No. 12/246,798 filed Jul. 10, 2008, which is a continuation-in-part of PCT Patent Application No. PCT/CA2007/000579 filed Apr. 5, 2007, which claims priority from U.S. Provisional Patent Application No. 60/789,891 filed Apr. 7, 2006, all of which are incorporated by reference herein.

FIELD OF THE INVENTION

The present invention relates to an apparatus for performing bone augmentation procedures, and more particularly to a cement delivery system for such procedures and to a method for the use of such a system.

BACKGROUND ART

A number of different types of bone cement injection procedures are routinely practiced, among which is vertebroplasty.

Unfortunately, the pressure required to inject cement can easily reach values beyond human physical limit. A number of pressure-controlled devices are available to increasing the pressure applied to the cement for delivery, however such devices may increase the risk of cement leakage because of a lack of control on the cement flow rate. It is also known to lower the cement viscosity to ease the injection, however such an approach may also generally increase the risk of cement leakage.

While most cement leaks are inconsequential, every leak nevertheless exposes patients to serious risks, such as spinal cord and nerve root compression, pulmonary embolism, and possibly even death.

Further, the viscosity of the bone cement changes as the cement polymerizes, while also varying substantially due to various factors such as environmental conditions (e.g. temperature, humidity), the mixing technique used, as well as the batch and type of cement used. Physicians often use suggestive methods such as visual and/or tactile inspection to evaluate whether the viscosity of cement is adequate for injection, such methods being generally imprecise and not easily reproducible.

Accordingly, improvements are desirable.

SUMMARY OF INVENTION

In accordance with the present invention, there is provided a bone cement delivery system for vertebroplasty comprising a rigid cannula having a tubular inner wall defining and surrounding a central conduit to deliver bone cement into a vertebra under pressure, the inner wall defining a distal outlet port of the central conduit at a distal end of the cannula, a tubular outer wall extending around the inner wall and spaced apart therefrom to define a peripheral conduit around the central conduit for aspirating bone fluids, the outer wall defining a distal inlet port of the peripheral conduit at the distal end of the cannula, the outer wall having an outer diameter not exceeding acceptable parameters for vertebroplasty, a proximal end of the cannula including a proximal inlet port in communication with the central conduit and a proximal outlet port in communication with the peripheral conduit, and aspirating means communicating with the proximal outlet port of the peripheral conduit to create a pressure gradient between the central conduit and the peripheral conduit to provide a hydraulic force guiding the displacement of bone fluid and the flow of cement.

Also in accordance with the present invention, there is provided a bone cement delivery system comprising a rigid cannula having a tubular inner wall defining and surrounding a central conduit for bone cement delivery, the inner wall defining a distal outlet of the central conduit at a distal end of the cannula, a tubular outer wall extending around the inner wall and spaced apart therefrom to define a peripheral conduit around the central conduit, the outer wall defining a distal inlet of the peripheral conduit at the distal end of the cannula, and a proximal end of the cannula including a proximal inlet port in communication with the central conduit and a proximal outlet port in communication with the peripheral conduit, and further comprising a tubular middle wall extending between the inner and peripheral walls and spaced apart therefrom to define a middle conduit around the central conduit, the peripheral conduit being defined around the middle conduit.

Also in accordance with the present invention, there is provided a medical cannula comprising at least one tubular wall defining and surrounding an injection conduit, the wall defining a distal outlet of the injection conduit at a distal end of the cannula, and a proximal end of the cannula including a proximal inlet in communication with the injection conduit, and an elastic and permeable membrane covering the distal outlet of the injection conduit for delivery of injected fluid therethrough.

Also in accordance with the present invention, there is provided a method of injecting bone cement within a vertebra, comprising injecting bone cement within the vertebra through a pedicle, and at least one of aspirating bone fluid from the vertebra through said pedicle simultaneously with the bone cement injection and creating a pressure gradient between the injection and aspiration steps to provide a hydraulic force guiding the displacement of bone fluid and the flow of bone cement.

Also in accordance with the present invention, there is provided a bone cement delivery device, comprising a syringe body for containing the bone cement, a plunger snuggly and slidably received within the syringe body for pushing the bone cement out of the syringe body, a driving system connected to the plunger and sliding the plunger within the syringe body, and a control system controlling the driving system in a displacement-controlled and continuous manner over a given time period to produce a constant flow of bone cement out of the syringe body within the time period based on commands from a user.

Also in accordance with the present invention, there is provided a bone cement delivery device comprising a body for containing the bone cement therein and for progressively injecting the bone cement therefrom for delivery into the bone, at least one sensor for measuring a physical parameter of the bone cement within the body, wherein the sensor is integral with the body, the at least one parameter being indicative of curing of the bone cement, and a display unit receiving data from the sensor and displaying at least one of the physical parameter and the curing progress of the bone cement.

Also in accordance with the present invention, there is provided a method of injecting bone cement within a bone, comprising monitoring at least one parameter indicative of a curing of the bone cement directly within a bone cement delivery device, and injecting the bone cement in the bone with the delivery device based on the at least one parameter.

Also in accordance with the present invention, there is provided a control system for a bone cement delivery device, the control system comprising a delivery pressure sensor for measuring a cement delivery pressure and producing corresponding delivery pressure data, a control panel for receiving commands from a user and producing corresponding command data, a driving system for actuating the cement delivery device to deliver the bone cement, a control module for receiving the command data and the delivery pressure data, and for sending a control signal actuating the driving system based on the command data and the delivery pressure data such as to deliver the bone cement in a steady flow, and a display unit for receiving the pressure data from the control module and displaying delivery pressure information based on the delivery pressure data.

Also in accordance with the present invention, there is provided an integrated cement delivery system comprising a cement delivery device including a syringe body for containing the bone cement, a plunger slidably received within the syringe body for pushing the bone cement out of the syringe body, and a driving system connected to the plunger and sliding the plunger within the syringe body, an injection pressure sensor measuring an injection pressure of the cement within the syringe body, a control system controlling the driving system in a displacement-controlled and continuous manner to produce a steady flow of bone cement out of the syringe body based on data from the injection pressure sensor and commands from a user, and a display unit displaying the data from the injection pressure sensor.

Also in accordance with the present invention, there is provided a method of extracting marrow from a vertebra, comprising injecting a thick liquid in the vertebra through a single pedicle, displacing the marrow with the thick liquid, and extracting the marrow through said single pedicle simultaneously with the thick liquid injection by creating a pressure gradient between the injecting and extracting.

Also in accordance with the present invention, there is provided a method of rinsing marrow within a vertebra, comprising inserting a cannula in the vertebra, injecting a liquid in the vertebra through a first conduit of the cannula, aspirating the marrow and bone fluid through a second conduit of the cannula and creating a pressure gradient between the first conduit and the second conduit.

Also in accordance with the present invention, there is provided, in combination, a cannula and a syringe body, the cannula defining an injection conduit having a constant diameter throughout a length thereof, and the syringe body includes a tapered distal end defining an outlet connected to the injection conduit of the cannula, the tapered distal end providing a progressive and constant diameter reduction between a remainder of the syringe body and the injection conduit.

Also in accordance with the present invention, there is provided a viscosity sensing unit for a bone cement delivery device, the unit comprising at least one sensor for measuring a physical parameter of the bone cement directly within the bone cement delivery device, the at least one parameter being indicative of a viscosity of the bone cement, and a display unit receiving data from the sensor and displaying at least one of the physical parameter and the viscosity of the bone cement.

Also in accordance with the present invention, there is provided a method for percutaneously preparing a bone at least partially filled with cancellous bone, comprising: percutaneously forming a path to the cancellous bone using a multi-lumen cannula having at least a central lumen and a concentric outer lumen; providing a first passage to the cancellous bone in the central lumen; providing a second passage in the concentric outer lumen; introducing a rinsing fluid in one of the first and second passages to rinse bone marrow and other soft tissue from the cancellous bone; and removing the rinsed bone marrow from the other of the first and second passages to form a region in the bone partially free of the bone marrow.

Also in accordance with the present invention, there is provided a method for percutaneously treating a tissue affected by a soft tissue, cystic or liquefied lesion, the method comprising: introducing a multi-lumen cannula in the tissue with the cannula having at least a central lumen and a concentric outer lumen; providing a first passage to the lesion in the central lumen; provided a second passage in an outer concentric lumen; introducing a rinsing fluid in one of the first and second passages to rinse the lesion; and removing the rinsed lesion from the other of the first and second passages.

Also in accordance with the present invention, there is provided a method of therapeutically or palliativelly treating tissue with a lesion, the method comprising: percutaneously forming a path to the lesion using a multi-lumen cannula; introducing a thick flowable material through a first lumen of the cannula to displace the lesion and tissue debris from the lesion; and applying suction through a second lumen of the cannula extending percutaneously into the lesion; wherein the suction being applied to the second lumen provides a hydraulic force guiding the displacement of the tissue debris and the flowable material.

Also in accordance with the present invention, there is provided a method of harvesting bone marrow, comprising: percutaneously introducing a multi-lumen cannula into a cancellous bone; applying suction through a first passage defined in a first lumen of the cannula; injecting a thick flowable material into the bone from a second passage in a second lumen of the cannula; extruding the thick flowable material through a distal end of the cannula into the cancellous bone in order to displace the bone marrow and other bone fluids, the suction applied through the first passage providing a hydraulic force guiding the displaced bone marrow; and collecting the displaced bone marrow for a therapeutic or diagnostic purpose.

Also in accordance with the present invention, there is provided a thick flowable material for use in harvesting bone marrow in the cancellous portion of a bone, the material having the following properties: the material forms a solid body at room temperature while below a yield stress of the material; the material is flowable when mechanical pressure causing a stress exceeding the yield stress is applied thereon; and the material becomes a solid body when the mechanical pressure is removed.

Also in accordance with the present invention, there is provided a method for percutaneously preparing a bone at least partially filled with cancellous bone in which bone marrow and other fluids are present, the method comprising: percutaneously forming a path to the cancellous bone using a multi-lumen cannula having at least a central lumen and a concentric outer lumen; forming a first passage to the cancellous bone in the central lumen; forming a second passage in the concentric outer lumen; introducing a catheter carrying an inflatable device at a distal end of the cannula through the first passage; inflating the inflatable device in the cancellous bone adjacent the distal end of the cannula, including displacing the bone marrow with the inflated device; and while the inflatable device is inflated, applying a negative pressure through the second passage to remove the displaced bone marrow and other fluids, and to reduce an embolic load related to the procedure.

Also in accordance with the present invention, there is provided a multi-lumen cannula for percutaneously preparing and/or treating body tissue, comprising: a first tubular wall having a distal end and defining a central conduit; a second tubular wall having a distal end, the second tubular wall concentric with the first tubular wall and defining an annular peripheral conduit around the central conduit; a shaftless helical screw extending in one of the central conduit and the peripheral conduit, coaxially with the tubular walls, the helical screw including a continuous helical blade with a helical edge proximate a respective one of the tubular walls; wherein the helical screw is configured to deliver a thick flowable material through to the distal end of the one of the central conduit and the peripheral conduit.

Also in accordance with the present invention, there is provided a multi-lumen cannula for percutaneously preparing and treating a body tissue, the cannula having a proximal end and a distal end and comprising: a rigid outer tube; an inner tube concentric with the rigid outer tube defining a first conduit therein and a second conduit between the outer tube and the inner tube; a delivery screw extending in the second conduit between the inner tube and the outer tube for injecting a thick flowable material through the second conduit to the distal end of the cannula; the inner tube having a distal portion extending beyond a distal end of the outer tube and the delivery screw, the distal portion defining openings for allowing tissue fluid to pass through to the first conduit; an aspirator connected to a port at the proximal end of the cannula; wherein the distal portion of the inner tube is intended to penetrate a lesion in a body tissue in order to aspirate the tissue fluids under the urging of the aspirator and the displacement thereof by the thick flowable material delivered by the delivery screw.

Also in accordance with the present invention, there is provided a cannula for percutaneously preparing and/or treating body tissue, comprising: a tubular wall defining a central conduit, the central conduit configured to form a path body tissue; a shaftless helical screw extending in the central conduit, coaxially with the tubular wall, the helical screw including a continuous helical blade with a helical edge proximate the tubular walls; wherein the helical screw is configured to percutaneously deliver a thick flowable material through to a distal end of the central conduit.

BRIEF DESCRIPTION OF THE DRAWINGS

Reference will now be made to the accompanying drawings, showing by way of illustration particular embodiments of the present invention and in which:

FIG. 1 is schematic representation of a cement delivery system according to a particular embodiment of the present invention;

FIG. 2 is a tridimensional cross-sectional view of a cannula according to a particular embodiment of the present invention;

FIG. 3 is a tridimensional cross-sectional view of a cannula according to an alternate embodiment of the present invention;

FIG. 4 is a side cross-sectional view of a screw delivery mechanism of the cannula of FIG. 3 according to a particular embodiment of the present invention;

FIG. 5A is a side cross-sectional view of a cannula according to an alternate embodiment of the present invention;

FIG. 6 is tridimensional view of a proximal end of a cannula, which may be for example the cannula of any one of FIGS. 2 to 5C, including a membrane according to a particular embodiment of the present invention;

FIG. 7 is a schematic tridimensional view of a proximal end of a cannula, which may be for example the cannula of any one of FIGS. 2 to 5C, including an intravertebral pressure sensor according to a particular embodiment of the present invention;

FIG. 8 is a schematic side view of a cement delivery device according to a particular embodiment of the present invention;

FIG. 9 is a schematic side view of a cement delivery device according to an alternate embodiment of the present invention;

FIG. 10 is a schematic side view of a cement delivery device according to an alternate embodiment of the present invention;

FIG. 11 is a schematic side view of a syringe and cannula assembly according to a particular embodiment of the invention;

FIG. 12 is a schematic side view of a syringe including injection pressure sensors according to a particular embodiment of the present invention;

FIGS. 13A-13C are schematic front views of syringes including different ultrasound viscosity sensors according to alternate embodiments of the present invention;

FIG. 14 is a tridimensional schematic view of a syringe including a dielectric viscosity sensor according to an alternate embodiment of the present invention;

FIG. 16 is a graphical representation of an example of the Root Mean Square of an ultrasound pulse of the ultrasound sensors of FIGS. 13A-13C;

DETAILED DESCRIPTION OF PARTICULAR EMBODIMENTS

Figure 5B:
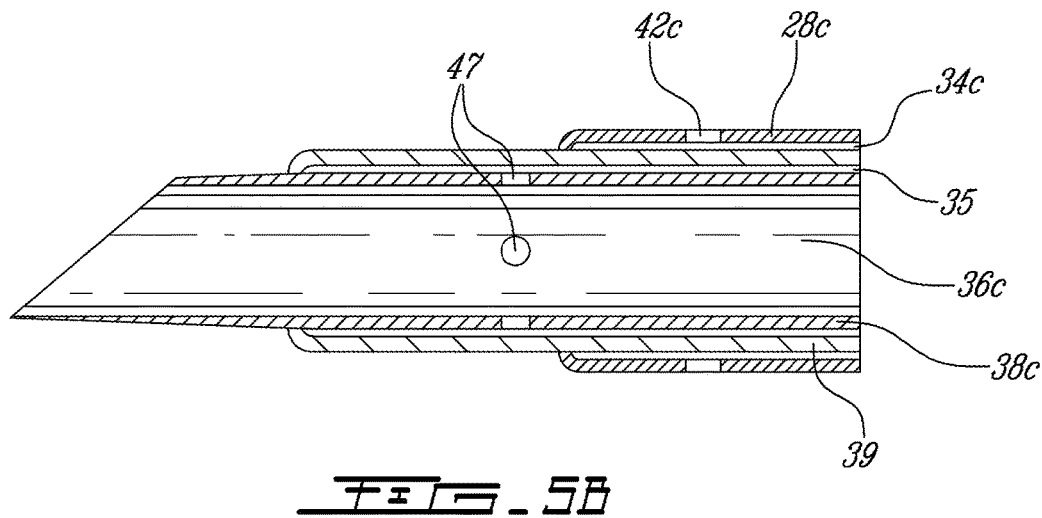
FIG. 5B is an enlarged, side cross-sectional view of a portion of the cannula of FIG. 5A.

Referring generally to FIG. 1, a cement delivery system according to a particular embodiment of the present invention is generally and schematically shown at 10. The system 10 generally comprises a cannula 12 which may include pressure sensors 14 to measure the intravertebral pressure, an assisted cement delivery device 16 delivering cement through the cannula 12 and including miniature viscosity sensors 18 to monitor a viscosity of the cement, a controller or control module 20, such as for example provided in an electronic circuit board including a microprocessor, for controlling or operating the cement delivery device 16, a digital display unit 22 for displaying sensor data during the procedure, a control or regulation panel 24 for receiving instructions from a user, and a power supply 26 providing power to the system 10.

The different elements of the cement delivery system 10 are separately described in more detail in the following.

Cannulae 12

The cannula 12 in FIG. 1 can be a standard cannula or, alternately, one of the cannulae 12a,b,c shown in FIGS. 2 to 7. The cannulae 12a,b,c described below allow for monitoring of the intravertebral pressures and/or aspiration of the vertebral body to drain the bone fluid (e.g. marrow, blood) that is displaced during the cement injection, such as to reduce cement leakage and reduce the risk of emboli. The cannulae 12a,b,c are preferably made of an appropriate type of metal or other rigid material, similarly to known single conduit cannula typically used in bone cement injection procedures.

In the case of vertebroplasty, the total pressure required for cement injection $\Delta p_{inj}$ can be separated into the extravertebral cement delivery pressure $\Delta p_{extra}$ required to force the cement through a cannula, the intravertebral cement infiltration pressure $\Delta p_{inf}$ required to force the cement to penetrate the vertebral cavity, and the intravertebral bone marrow pressure $\Delta p_{mar}$ within the vertebral body due to the hydraulic resistance of the vertebra, i.e. $\Delta p_{inj} = \Delta p_{extra} + \Delta p_{inf} + \Delta p_{mar}$. The extravertebral delivery pressure $\Delta p_{extra}$ is generally the largest (e.g. up to 500 psi for mechanical injectors), while the infiltration pressure $\Delta p_{inf}$ and the bone marrow pressure $\Delta p_{mar}$ are generally much lower (e.g. 50 psi and 5 psi, respectively).

Monitoring of the internal bone pressure, or, in the case of vertebroplasty, of the intravertebral pressure (i.e. the infiltration pressure $\Delta p_{inf}$ and the bone marrow pressure $\Delta p_{mar}$) ensures that there is no excess pressure in the bone (vertebral) cavity when delivering cement, as an elevated pressure may cause the cement to spread suddenly in uncontrolled fashion or cause lung emboli. The monitoring of the internal or intravertebral pressure can also be used as a predictor of leakage, since a sudden pressure drop may indicate the existence of a path of least resistance leading to cement leakage. The monitoring of the internal or intervertebral pressure thus allow for prevention of these complications.

Knowledge of the internal or intravertebral pressures also allows for the determination of the pressure within the cannula (e.g. extravertebral), which creates a diagnostic tool for the case in which the physician is not in a position to deliver cement, for example indicating that the cannula is plugged or that the cement is not going into the bone (vertebral body).

Referring to FIG. 2, the cannula 12a includes an outer tubular wall 28a defining a proximal end 30 and a distal end 32. Concentric peripheral and central conduits 34a, 36a are separated by a thin tubular internal wall 38a extending in the cannula 12a spaced apart from the outer tubular wall 28a. The cannula 12a includes a side outlet 40a defined at the proximal end 30 and a series of fenestrations 42a defined at the distal end 32, both of which being in communication with the peripheral conduit 34a. The central conduit 36a is used to deliver the cement, while the peripheral conduit 34a is used to aspirate the vertebra to aspirate bone fluid (e.g. marrow, blood) during cement injection, or to measure the intravertebral cement infiltration or bone marrow pressures $\Delta p_{inf}$ or $\Delta p_{mar}$ through a pressure sensor 14 (see FIG. 1).

In the case where the peripheral conduit 34a is used to aspirate the vertebra, the fenestrations 42a represent a vent or a sink for the displaced bone fluid when the cement enters the vertebral cavities. In a particular embodiment, the aspiration is done manually using a standard syringe attached to the side outlet 40a to create a vacuum while the physician delivers the cement and to remove the bone fluid. In a more preferred embodiment, the aspiration is done in an automated manner and more specifically, in a volume controlled manner. The automated aspiration allows for cement to be injected at a given flow rate and for bone fluid to be aspirated at a slightly higher flow rate, such that the cement follows the displaced bone fluid and takes its place. One practical way of producing the vacuum for the automated aspiration is to use a vacuum pump connected to the side outlet 40a and applying for example a low-level vacuum in the range of 10 to 100 kPa. The vacuum pump is preferably regulated by a vacuum regulator (e.g. mechanical or electronic), which is regulated by the control module 20 as will be described in a following section.

In addition to removing bone fluid, the aspiration or vacuum creates a pressure gradient between the central conduit 36a and the peripheral conduit 34a, which creates a hydraulic force guiding the displacement of the bone fluid and the flow of the cement. This pressure gradient can be used to guide the cement flow to facilitate controlled and predictable filling with enhanced mechanical efficacy and reduced cement emboli.

In a particular embodiment where the peripheral conduit 34a is used to measure the intravertebral cement infiltration or bone marrow pressures $\Delta p_{inf}$ or $\Delta p_{mar}$, the pressure sensor 14 (see FIG. 1) is provided at the proximal end of the peripheral conduit 34a, and either air or liquid is used as a media to transfer the pressure wave generated in the vertebra when delivering cement from the distal end 32 of the cannula to the pressure sensor 14.

The cannula 12a may feature different fenestration patterns at its distal end 32 that that shown in order to meet different functions.

The cannula 12b shown in FIG. 3 is similar to the cannula 12a, and includes an outer tubular wall 28b, concentric peripheral and central conduits 34b, 36b separated by a thin tubular internal wall 38b spaced apart from the outer tubular wall 28b, as well as a side outlet 40b at the proximal end 30 and a series of fenestrations 42b at the distal end 32 which are both in communication with the peripheral conduit 34b. Like the cannula 12a, the central conduit 36b of the cannula 12b is used to deliver the cement while the peripheral conduit 34b is used to aspirate and drain the bone fluid as described above, or to measure the intravertebral cement infiltration or bone marrow pressures $\Delta p_{inf}$ or $\Delta p_{mar}$ through a pressure sensor 14 (see FIG. 1).

However, the cannula 12b also includes a side inlet 41 defined at the proximal end 30 in communication with the central conduit 36b, through which the cement enters the cannula 12b. The cannula 12b additionally includes a screw delivery mechanism 43 extending within the central conduit 36b along its length. In a particular embodiment, the screw delivery mechanism 43 is either a helical or spiral transport screw. The rotating screw delivery mechanism 43 facilitates the transport of the cement through the central conduit 36b in a precise manner.

The cannula 12b is thus especially useful for injecting cements that are difficult to inject because of phase separation, such as for example calcium phosphate (CaP), with the screw delivery mechanism 43 increasing the mixing of the cement to reduce the risk of phase separation. The screw delivery mechanism 43 also significant decreases the pressure required for cement delivery since the cement delivery by the screw delivery mechanism 43 requires little pressure when compared with simply pushing the cement though the elongated geometry of the cannula, and as such can also be used to transport thick PMMA cement. The use of thick cement reduces the risk of leakage, while the use of the screw delivery mechanism 43 facilitates the cement delivery without the need for excessive forces.

Although the rotation of the screw delivery mechanism 43 can be applied manually, in a particular embodiment the rotation is applied by a micro motor (not shown). As such, the pressure drop in the cannula 12b is overcome by the power of the micro-motor and the physician does not contribute to overcoming this pressure. The rotation speed of the screw delivery mechanism 43 is regulated, for example by the control module 20 as will be further described below, to adjust for the desired delivery flow rate. As such, the physician can shift focus on the patient and on the surgery instead on being focused on delivering sufficient cement in the intervention. In a particular embodiment, where the central conduit 36b and screw 43 are designed for cement delivery at a speed 3 ml/minute, the micro-motor rotating the screw delivery mechanism 43 provides a power of approximately 52 mW.

In a particular embodiment, the screw delivery mechanism 43 is a typical delivery screw. However, in an alternate embodiment shown in FIG. 4, the screw delivery mechanism 43 is cannulated, i.e. an inner conduit 37 is defined within the screw delivery mechanism 43 along its length. This inner conduit 37 is preferably instrumented to measure the intravertebral cement infiltration pressure $\Delta p_{inf}$, with either air or liquid being used for the transfer of the infiltration pressure from the distal end of the screw to the proximal end of the screw, where a pressure sensor 14 (see FIG. 1) is mounted. The screw 43 may additionally feature radial fenestrations or vents that connect directly to its inner conduit 37. The peripheral conduit 34b is used to measure the intravertebral bone marrow pressure $\Delta p_{mar}$ or to aspirate the bone fluid as the bone cement is delivered through the central conduit 36b.

Figure 5C:
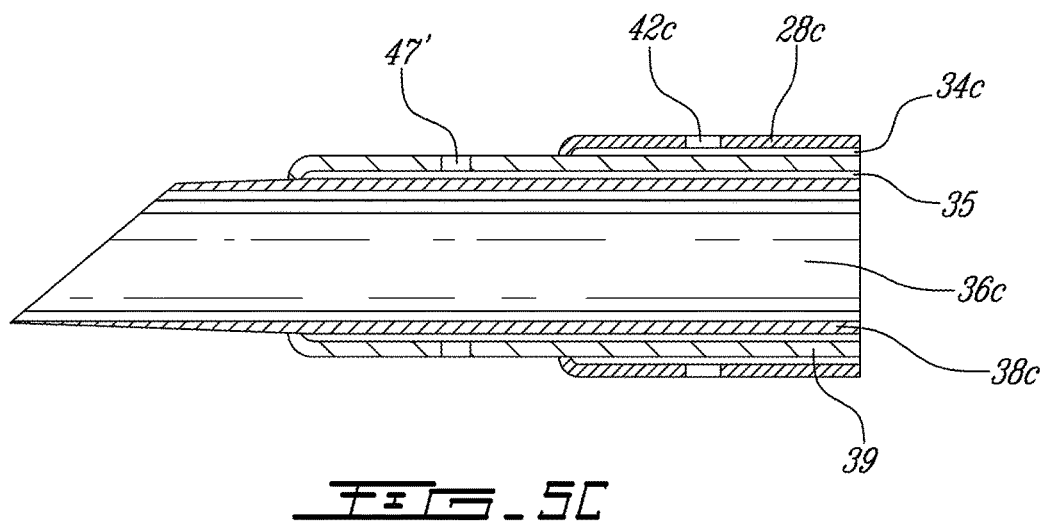
FIG. 5C is an enlarged, side cross-sectional view of a portion of the cannula of FIG. 5A according to an alternate embodiment of the present invention.

The cannula 12c shown in FIGS. 5A-5C includes concentric tubular inner, middle and outer walls 38c, 39, 28c, thus defining central, middle and peripheral concentric conduits 36c, 35, 34c. A side outlet 40c (see FIG. 5A) defined at the proximal end 30 and a series of fenestrations 42c (see FIGS. 5B-5C) at the distal end 32 are both in communication with the peripheral conduit 34c. A second side outlet 45 defined at the proximal end is in communication with the middle conduit 35. The central conduit 36c is used to deliver bone cement.

Referring particularly to FIG. 5B, in one embodiment, fenestrations 47 are defined through the inner wall 38c, and the middle conduit 35 is used to measure the intravertebral cement infiltration pressure $\Delta p_{inf}$ while the peripheral conduit 34c is used to aspirate the bone fluid or to measure the intravertebral bone marrow pressure $\Delta p_{mar}$. As described above, in a particular embodiment a pressure sensor 14 (see FIG. 1) is mounted to the proximal end of the middle conduit 35 and either air or liquid is used as a media to transfer the pressure wave generated in the vertebra when delivering cement from the distal end 32 of the cannula to the pressure sensor 14.

In another embodiment shown in FIG. 5C, the fenestrations 47' are alternately defined through the middle wall 39, and one of the middle and peripheral conduits 35, 34c is used to measure the intravertebral bone marrow pressure $\Delta p_{mar}$ while the other is used to aspirate the bone fluid.

Alternately, the screw delivery mechanism 43 of the cannula 12b, with or without its inner conduit 37, can be integrated in a single conduit cannula or in a cannula having three conduits such as 12c.

The cannulae 12a,b,c thus allow for the bone fluid to be aspirated and the cement to be injected simultaneously and using a same operative site, without the need to use separate cannulae, which reduces the risks of complications.

The cannulae 12a,b,c can also advantageously be used to rinse the bone marrow and create a path favoring cement flow. Prior methods of rinsing the bone marrow usually necessitate the use of two separate surgical sites. With the cannulae 12a,b,c, pulsating or non pulsating fluid is injected through one of the conduits, creating a pressure gradient between the conduits and allowing for the rinsing process to be performed using a single cannula and thus a single surgical site. The rinsing process is done manually or automatically with the help of an automated system, applying a level of pressure similar to the one applied for bone fluid extraction. In an alternate embodiment, the rinsing process is performed through a smaller diameter tubing extending within the cannula (either 12a,b,c or single conduit cannula) extending deeper within the vertebra.

FIG. 6 shows a membrane 44 which is optionally attached at the distal end 32 of the central conduit 36a,b,c of any one of the cannulae 12a,b,c described above or, alternatively, at the distal end of a single conduit cannula. The membrane 44 is preferably elastic and retractable, and has a permeability (illustrated by holes 46) that is roughly ten percent (10%) of the permeability of osteoporotic cancellous bone. The size and elasticity of the membrane 44 is preferably such as to define an expanded diameter of no more than 5 millimeters to ensure the least damage to the surrounding bone. The membrane 44 can be made of fabric tissue or preferably super elastic metals.

When the cement is delivered, it expands the membrane 44 and generates a state of uniform hydrostatic pressure inside the membrane 44. Specifically, the rate of cement flow exterior to the membrane 44 is controlled by the pressure gradient between the membrane 44 and the surrounding bone. The intravertebral pressure in the surrounding bone is insignificant, thereby imposing a constant uniform pressure gradient on the surface of the membrane 44. This uniform gradient leads to uniform and controlled flow of the cement through the membrane 44 and in the environment. The membrane 44, due to the low permeability, is thus the guiding tool for the intravertebral flow. Thus, the membrane 44 ensures controlled slow and uniform expansion of the cement, and prevents preferential pressure gradients caused by local bone morphology and thereby, ensuring seepage flow and likely reducing leakage risk.

In the case where the internal bone pressure (e.g. intervertebral pressure) is not measured through a separate conduit of the cannula, the cannula preferably includes a pressure sensor 14 as shown in FIG. 7, such as a miniature MEM sensor, which is placed directly at its distal end 32 while ensuring that the flow is not obstructed. This provides direct readings of the internal or intravertebral pressure during the cement delivery process.

As mentioned above, any one of the cannulae 12a,b,c can take the place of the cannula 12 in the cement delivery system shown in FIG. 1. The cannulae 12a,b,c present the advantage of allowing for multiple operations (cement delivery and pressure measurements and/or bone marrow extraction and/or bone marrow rinsing) using a single site.

Although the cannulae 12a,b,c have been described mostly with relation to vertebroplasty, the cannulae 12a,b,c can alternately be used in other cement augmentation procedures where cement is injected into other anatomical locations (such as osteoporotic femur and distal radius) and where similar issues of high pressure exist. Additionally, the cannulae 12a,b,c can also be used in any appropriate type of percutaneous injection of viscous biomaterials into the human body (e.g., drug delivery using carriers, biometrices for tissue engineering).

In addition, the cannulae 12a,b,c can advantageously be used for bone marrow extraction for graft, blood disorders, stem cell transplantation or orthopedic procedures. Known methods of performing bone marrow extraction include directly using a syringe to remove the bone marrow, generally extracting mostly blood and a small quantity of marrow. With the cannulae 12a,b,c, a thick liquid is delivered through one of the conduits, invading the bone cavity saturated by bone marrow and as such displacing the bone marrow, which is then guided through suction into another conduit of the cannula, thus increasing the efficiency of the bone marrow extraction procedure.

Cement Delivery Device 16

It has been shown that when a fairly liquid cement is injected into a vertebra, the cement finds and flows through a path of least resistance, however when the cement is injected at a viscosity or degree of curing that is high enough, it expands uniformly as if the path of leakage did not exist. Accordingly, by controlling the time of injection and thereby the cement viscosity, the incidence of leakage can be reduced considerably. The challenge is that cement generally ceases to be manually injectable with a standard syringe and cannula at about the minimal viscosity avoiding flowing through the path of least resistance.

Referring back to FIG. 1, the cement delivery device 16 generally includes a syringe body 58 and a syringe plunger 60 which is displaced within the body 58 by any adequate driving system 62, such as for example an electric motor, a pneumatic system or an hydraulic system. The driving system 62 is controlled or regulated by the control module 20, as will be described in a following section, such that the displacement of the plunger 60 is controlled, preferably advancing in a continuous manner (i.e. in a consecutive series of steps of equal duration and equally spaced apart, or with an uninterrupted motion at a constant speed) in the syringe body 58, such as to precisely deliver a given volume of cement, thus reducing undesired excess cement which increases leakage risks. In a particular embodiment, the driving system 62 allows for the delivery of a desired volume of cement with a precision of 50 micro liters. The driving system 62 generates an axial force on the plunger 60 which generates an injection pressure substantially greater than human physical limits and sufficient to deliver the cement, thus overcoming the limitation of excessive pressure and increasing the chances of being able to complete the procedure adequately. In a particular embodiment, the axial force generated by the driving system 62 is approximately 2 KN. The increased injection pressure ensures the delivery of thicker cement, which substantially reduces the risks of cement leakage.

The driving system 62 delivers the cement continuously and slowly, for example at 3 ml/minute, and in a particular embodiment, at most 10 ml/minute, resulting in a steady flow which enhances cement filling uniformity and reduces leakage risks by reducing undesired transient peaks in pressure.

The driving system 62 allows for a displacement controlled delivery which leads to stable flow conditions, thereby reducing the risk of sudden uncontrolled flow in the case of leakage.

Referring to FIG. 8, a particular embodiment 16a of the cement delivery device 16 is shown. The cement delivery device 16a includes a worm gear speed reduction mechanism 64 connected to the driving system 62, depicted here as an electric motor. The motor 62 powers the endless screw component 66 of the worm gear mechanism 64, which turns the wheel component 68 that rotates a threaded rod 70a. The threaded rod 70a is rotationally supported between two supports 72, which also support a guidance rod 74 extending therebetween. A nut 76 is slidably retained by the guidance rod 74 and threadingly engaged to the threaded rod 70a. The rotation of the threaded rod 70a causes a lateral motion of the nut 76 and of a pushrod 78a connected thereto, the pushrod 78a activating the movement of the syringe plunger 60 within the body 58 of the syringe 114 to inject the cement. The guidance rod 74 ensures steady movement of the pushrod 78a for accurate cement delivery.

A number of alternate embodiments are possible. For example, in one alternate embodiment, the nut 76 is omitted, and the rotation of the threaded rod 70a directly applies a lateral force to the pushrod 78a which is threadingly engaged therewith and slidably received on the guidance rod 74. In another alternate embodiment, the pushrod 78a is omitted, and the nut 76 directly activates the movement of the plunger 60. In another alternate embodiment, the guidance rod 74 and pushrod 78a extend on opposed sides of the syringe body 58 for improved stability. In another alternate embodiment, the supports 72 can directly support and guide the threaded rod 70a, pushrod 78a and/or nut 76, and as such the guidance rod 74 can be omitted. In another alternate embodiment, the pushrod 78a or the nut 76 acts directly as the syringe plunger 60, thus reducing the number of necessary elements. Other modifications are also possible.

Referring to FIG. 9, another particular embodiment 16b of the cement delivery device 16 is shown. The cement delivery device 16b includes a spur gear and toothed rack speed reduction mechanism 82 connected to the driving system 62, shown here as an electric motor, through a pinion 80. The motor 62 rotates the pinion 80, which rotates the spur gear 84 of the mechanism 82, which in turn forces the movement of the toothed rack 86. The rack 86 is fixed to the pushrod 78b, so the movement of the rack 86 applies a lateral force to the pushrod 78b which activates the movement of the syringe plunger 60 inside the body 58 of the syringe 114 and forces the injection of the cement.

Referring to FIG. 10, another particular embodiment 16c of the cement delivery device 16 is shown. The cement delivery device 16c is simple and the driving system 62, whether electrical, pneumatic, hydraulic or other, is a linear motor, directly rotating and translating a threaded rod 70c. The threaded rod 70c is attached to an interchangeable head 88 that acts as the plunger 60 within the body 58 of the syringe 114. The lateral movement of the head 88 forces the injection of the cement.

Accordingly, any one of the devices 16a,b,c can take the place of the cement delivery device 16 in the cement delivery system 10 shown in FIG. 1.

Any one of the devices 16a,b,c can also be used in any appropriate orthopedic application where medical cement is injected.

Referring to FIG. 11, as suddenly contracting geometry from the cement delivery device 16 to the cannula 12 in conventional procedures can causes a substantial increase in injection pressure, in a particular embodiment the geometrical transition from the device 16 to the cannula 12, 12a,b,c is adapted, thereby minimizing unnecessary pressure loss. The diameter of the central conduit 36a,b,c of the cannula is constant, even in its proximal end 30, where the outer tubular wall 28a,b,c defines a connection element 87 such as for example a male Luer lock adapter. The syringe body 58 is tapered, for example defining a conical shape extending at an angle $\alpha$ (which in a particular embodiment is approximately 45°) from a remainder of the syringe body 58, up to a complementary connection element 89, such as for example a complementary female Luer lock adapter, surrounding the connection element 87 of the cannula 12, 12a,b,c. This provides a smooth transition between the diameter of the major part of the syringe body 58 and the constant diameter of the central conduit 36a,b,c, thus lowering the overall injection pressure, and as such facilitating the delivery of thicker cements. Such a connection can alternately be used in other types of syringes and delivery systems for cements or other thick medium, including manual delivery systems.

Referring to FIG. 12, in a particular embodiment the cement delivery device 16 (16a,b,c, or other) is instrumented to measure the injection pressure. The device 16 comprises injection pressure sensors 90 including a strain gauge bridge 92 embedded directly in the syringe plunger 60, such as to measure the overall injection pressure during the cement delivery process. In an alternate embodiment, the injection pressure sensors 90 include a force or loading cell embedded between the plunger and the displacing mechanism of the plunger. An example for such a load cell is a cylindrical load cell with two threads protruding from both sides.

The injection pressure can be calculated once the injection force and the cross-sectional area of the syringe are known. The injection pressure sensors 90, whether in the form of force sensors or in any other adequate form, can alternately be included in any other appropriate location of the cement delivery device 16, 16a,b,c, such as for example within the driving system 62.

With the knowledge of the injection pressure and of the internal bone pressure (e.g. intravertebral), the pressure drop in the cannula 12 can be determined, and as such, based on the known injection speed and cannula dimensions, the viscosity of the cement can be determined through Hagen-Poiseuille's law.

Viscosity Sensor 18

As shown in FIG. 1, the cement delivery system 10 further includes viscosity sensors 18 providing continuous viscosity or curing readings of the polymerizing cement in the cement delivery device 16, without introducing any significant changes to the technique of vertebroplasty.

The role of cement viscosity or the degree of polymerization plays a significant part in the safety of vertebroplasty. More specifically, cement having a higher viscosity enhances the uniformity of the cement filling, thereby reducing the risk of cement leakage. Specifically, the viscosity sensors 18 monitor changing physical properties triggered by the cement polymerization. In particular embodiments, the sensors monitor acoustic properties of the cement, while in alternate embodiments the sensors monitor electrical properties of the cement. Alternately, other properties of the cement can be monitored, for example using piezo-electric sensors, a conductive grid, photonic sensors, reflective sensors, spectroscopic sensors, etc. The viscosity sensors 18 can be used in vertebroplasty but also in cement guns or delivery systems used in arthroplasty, or in any medical intervention where bone cements are used and where physicians require cement viscosity readings.

In particular embodiments shown in FIGS. 13A-13C, the miniature viscosity sensors 18a,b,c include an ultrasound emitter 94a,b,c and an ultrasound receiver 96a,b,c positioned around the syringe body 58. The emitter 94a,b,c sends out an ultrasound signal that goes through the cement and reaches the receiver 96a,b,c. The sensors 18a,b,c measure the pulse attenuation, time delay, traveling speed, and the intensity of the ultrasound signal. These quantities change as the cement polymerizes in the syringe body 58. When these readings are known, the cement properties are determined accurately. The sensors 18a,b,c are non-invasive and non-intrusive, forming an integral and reusable part of the cement delivery system 10. The ultrasound signal can be longitudinal or transversal.

In the embodiment shown in FIG. 13A, both the emitter 94a and receiver 96a of the sensor 18a are integrated into one unit. In the embodiment shown in FIG. 13B, the emitter 94b and receiver 96b of the sensor 18b are two isolated entities or components that are located at the opposite sides of the syringe body 58. In the embodiment shown in FIG. 13C, the receiver 96c and emitter 94c are positioned at two different locations one a same side of the syringe body 58.

The initial pulse and the attenuated pulse are triggered, controlled or regulated and analyzed by the control module 20 (see FIG. 1), as will be described in a following section.

The display unit 22 (see FIG. 1) displays various information obtained from the sensors 18a,b,c, which include for example: the attenuation or dampening of the original signal compared to the received signal, the velocity at which the signal travels through the cement, the delay time which is the time taken by the pulse to travel through the cement, and the Root mean square (RMS) which measures the intensity of the received signal. The delay time and the velocity are interrelated because of the fixed diameter of the syringe.

Figure 15A:
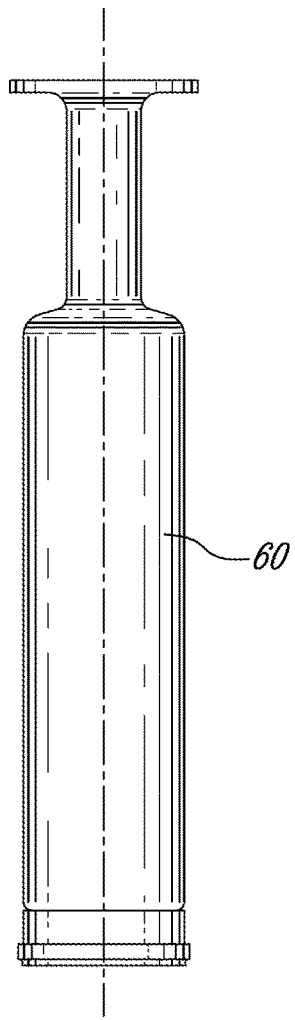
FIGS. 15A-15B are front and bottom schematic views of a syringe plunger including a dielectric or electro-resistive viscosity sensor according to an alternate embodiment of the present invention.
Figure 15B:
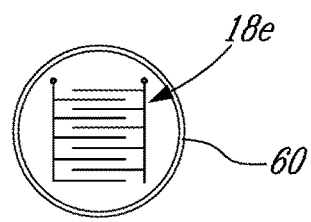

In alternate embodiments shown in FIGS. 14-15 the miniature viscosity sensors 18d,e include dielectric or electro-resistive sensors. The dielectric sensors measure the capacitive and conductive properties of the polymerizing cement, and the electro-resistive sensors measure the resistive properties of the cement. An advantage of the dielectric and electro-resistive sensors is that they can be integrated in the electronic circuit board including the control module 20.

In the embodiment shown in FIG. 14, the dielectric sensor 18d is reusable and is an integral component of the cement delivery system 10. This sensor 18d comprises two thin metallic plates 98 with a convex geometry, or any other appropriate geometry, adapted to partially surround the syringe body 58 and defining a capacitor or condenser. The two plates 98 are spring loaded through springs 100. Once the standard syringe body 58 is placed between the two plates 98, the springs 100 clamp the syringe body 58 and ensure direct physical contact between the two plates 98 and the syringe body 58 filled with the cement. An alternating current is sent through the two plates 98 and the reading of the capacitive and conductive changes on the digital display provide information on the cement polymerization process.

In a particular embodiment, the syringe body 58 has an elliptical or rectangular cross-section, which increases the uniformity of the electric field and as such the stability of the measurements. The rectangular cross-section, or alternately, a square cross-section (the corners of which can be rounded to facilitate sealing with the plunger) advantageously increases the capacity and also provide the advantage of ensuring that the distance between the plates 98 is constant and known, which further increases the stability of the measurements. Alternately, the syringe body 58 can have a more standard round cross-section.

In an alternate embodiment, the plates are integrated into the standard syringe body 58, thereby leading to an instrumented disposable syringe. Electroless metallic coating can be used to coat the syringe body 58 to form the plates. The functional thickness of the plates is preferably no more than a few microns, mainly because of the capacitive and conductive changes that take place on the atomic level. In a non-invasive version of the sensor, the thin plates are placed on the outer surface of the syringe body 58, in a geometry similar to that of the plates 98 shown in FIG. 14 to define a capacitor or condenser. In an invasive version of the sensor, which can be either a dielectric or an electro-resistive sensor, the plates are positioned on the inner surface of the syringe body 58 (not shown) or on the tip of the plunger 60 to form the sensor 18e shown in FIG. 15. In both cases, the plates act as electrodes of the electro-resistive sensor or as a capacitor of the dielectric sensor. Such instrumented syringes can be produced on a large scale at reasonable cost.

For both reusable and disposable sensors, the electrical signals indicating the change in the capacitive and conductive properties or resistive properties of the cement is processed and analyzed by the control module 20, and displayed on the display unit 22 of the system 10 (see FIG. 1), as will be further detailed in a following section.

Any one of the viscosity sensors 18a,b,c,d,e can take the place of the viscosity sensor 18 of the cement delivery system 10 shown in FIG. 1.

The viscosity sensors 18a,b,c,d,e can define, together with the display unit 22, a viscosity sensing unit which can be used in any medical intervention where bone cements are used and where physicians require cement viscosity readings, and in combination with any other appropriate cement delivery device 16.

Ultrasound Miniature Viscosity Sensor Experiment

The ultrasound viscosity sensors 18a,b,c were tested according to the following. An ultrasound pulse was sent to a 10 cc syringe, and the Root Mean Square (RMS), attenuation, and the velocity were measured. We also examined the use of longitudinal versus transverse ultrasound waves in addition to two frequencies of 1 and 5 MHz, although it should be understood that other frequencies can be used. The emitter and receiver were positioned around the syringe using a custom made holder. A pulse generator was used to trigger the initial pulse. The attenuated pulse received was amplified and displayed on the oscilloscope. The data was processed and analyzed using a pc.

Figure 17:
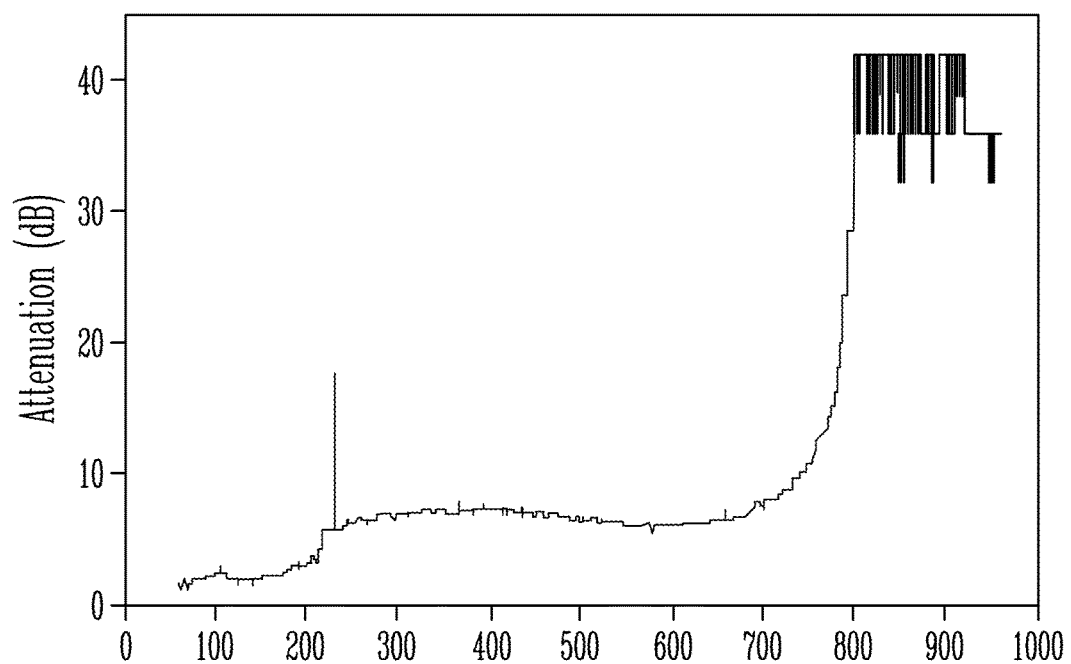
FIG. 17 is a graphical representation of an example of the attenuation of the ultrasound pulse of the ultrasound sensors of FIGS. 13A-13C.

The results of the experiment are shown in FIGS. 16-17. The times indicated in these figures represent the time after cement mixing. Time 0 is the point in time where the two components were mixed. Likewise, time 600 is ten minutes after cement mixing. FIG. 16 shows the evolutions of Root Mean Square (RMS) over the period of polymerization of the cement. The curve shows an initial plateau, followed by a significant drop and a slight increase. The curve also shows interesting features around 600 seconds and 800 seconds after the mixing. FIG. 17 shows the attenuation of the signal over time. Both figures show constant change up to roughly 7 minutes. Within two minutes thereafter, there is a significant increase because of the polymerization. Finally, the signal levels off. These two curves are similar to the viscosity curve or the heat production curve when testing cement in a rheometer or a calorimeter.

Dielectric Miniature Sensor Experiment

The dielectric viscosity sensors 18d,e were tested according to the following. In the reusable embodiment, a sensor was custom made to host the syringe filled with cement. In the disposable embodiment, a metallic coating was used to produce the plates on the outer surface of the syringe. Also, some measurements have been taken with an invasive disposable dielectric sensor. For the data acquisition, a RCL meter was used to replace the control module 20 of the system 10 and to measure the capacitive and conductive changes of the cement.

Figure 18:
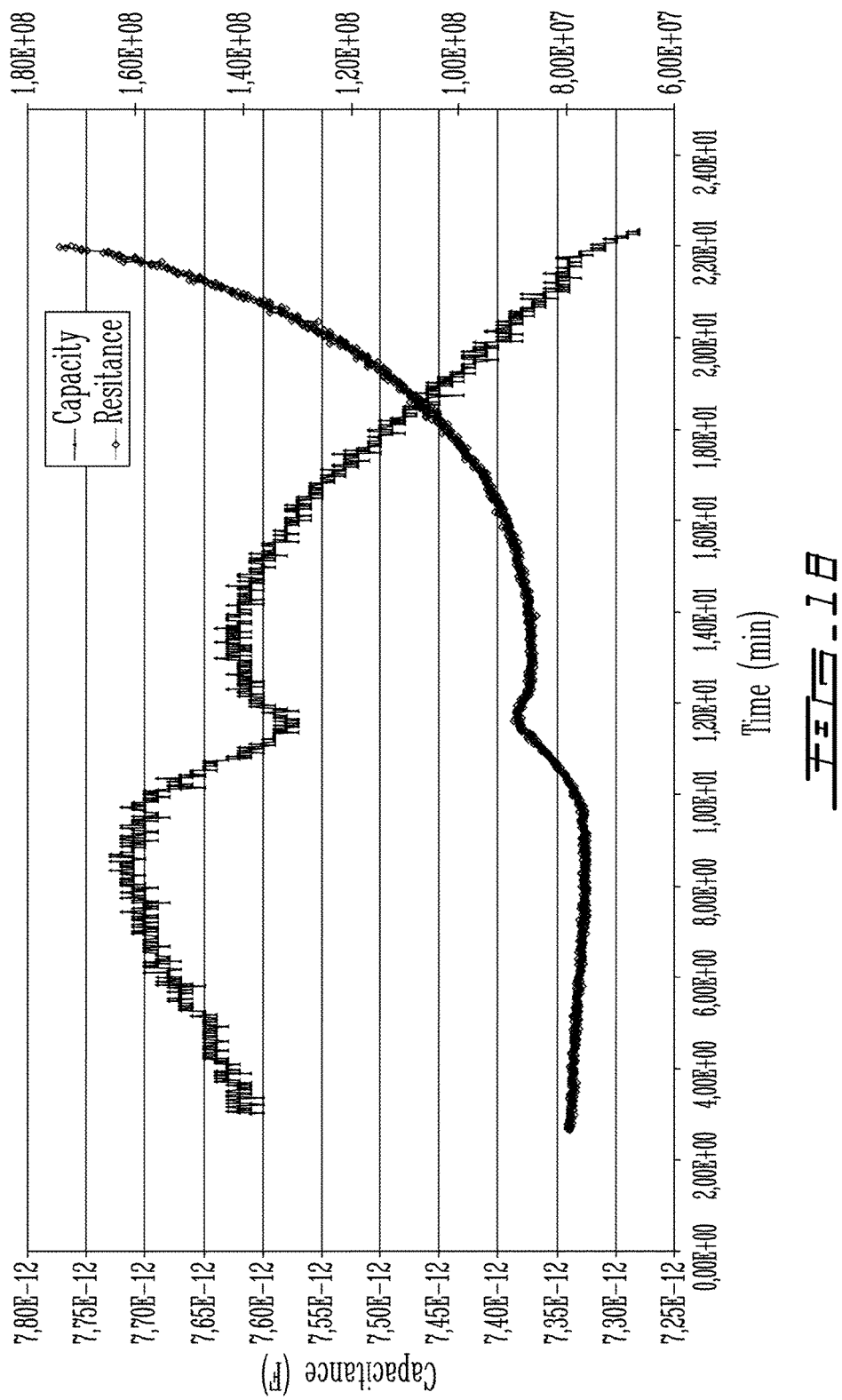
FIG. 18 is a graphical representation of an example of a capacity, resistance, impedance and phase of the dielectric sensors of FIG. 14.

The results are shown in FIG. 18, where the times depicted in the figures indicate the point in time after the cement has been mixed. FIG. 18 shows both the capacitive as well as the conductive changes measured when using the non-contact sensor. It is used as a representation of the results that can be obtained from a dielectric sensor. The figure depicts that significant changes in both capacitive and resistive changes take place as time proceeds and these changes are reproducible and can be used to monitor the advancement of cement polymerization.

Control System 102

Figure 19:
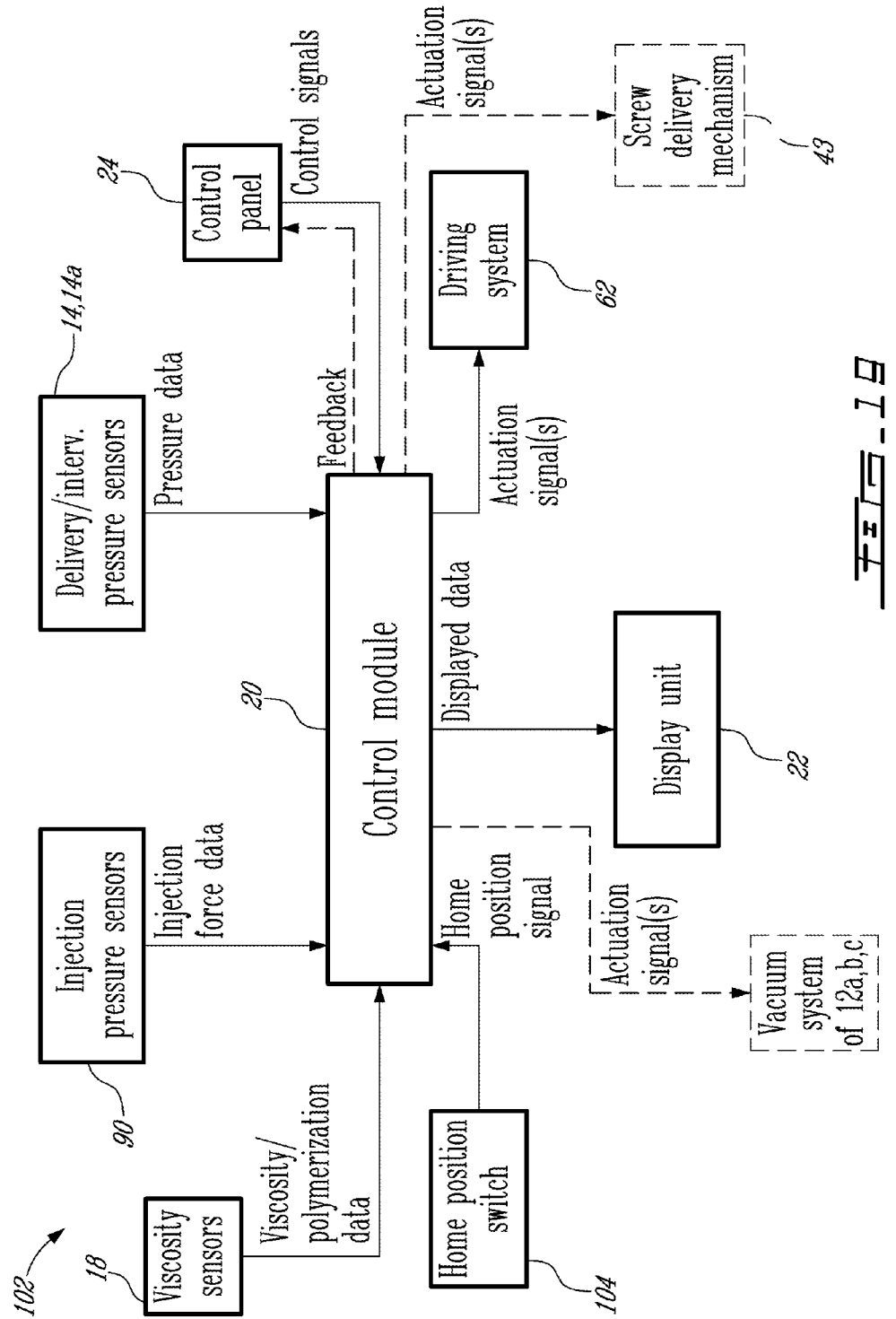
FIG. 19 is a block diagram of a control system according to a particular embodiment of the present invention.

Referring to FIG. 19, in a particular embodiment an integrated cement delivery system such as shown in FIG. 1 includes a control system 102. In a particular embodiment, the control system 102 allows the cement delivery system 10 to enhance the uniformity of the cement filling through the controlled injection of a cement of adequate viscosity in a precise and continuous manner, the regulation of the internal and injection pressures, the immediate depressurization of the vertebra, and the monitoring and feedback provided to the physician.

The control system 102 comprises the control module 20, the intravertebral pressure sensors 14, viscosity/curing sensors 18, injection pressure sensors 90, control panel 24 and a home position switch 104 all sending signals to the control module 20, and the display unit 22 and driving system 62 receiving signals from the control module 20. The home position switch 104 ensures the accurate positioning of the driving system 62. The switch 104 can be, for example, an optical sensor or a mechanical switch, or an external sensor attached to the cannula 12.

The digital display unit 22 is a tool to monitor the cement injection process. The display unit 22 displays data received from the control module 20 such as cement viscosity, total injection pressure, cannula delivery pressure, intravertebral pressure, cement delivery rate or speed, total injected volume, etc. All of these readings are displayed graphically and/or numerically. The display unit 22 can be integrated in the cement delivery device 16 as will be further detailed below. In addition or in the alternative, the display unit 22 can include an external large screen connected to the cement delivery device 16 for better display and readability.

In a particular embodiment, the control module 20 is provided by an electronic circuit board (not shown) including a microprocessor, the electronic circuit board having four objectives: (a) management of the power supply of the sensors 14, 18, 90 and the driving system 62; (b) gathering and processing signals and instructions from the sensors 14, 18, 90 and the physician; (c) advancing the syringe plunger 60 of the cement delivery device 16; and (d) outputting signals for the display unit 22. The electronic circuit board uses the external power supply 26 (see FIG. 1) for objective (a), which in the embodiments shown is a DC power supply of 24V/1.5-3A. The control module 20 performs the other objectives.

In particular embodiments, the control module 20 has the additional objective of controlling the vacuum applied to the cannula 12a,b,c for bone fluid extraction through a vacuum regulator such as to synchronize the bone fluid extraction with the cement injection, and/or controlling the micromotor rotating the screw delivery mechanism 43 of the cannula 12b.

In the case where a pneumatic or hydraulic cement delivery device 16 is used, the control module 20 regulates the cement delivery process through adequate proportional, differential or integral mechanisms for regulation.

In the embodiment shown, the inputs of the control module 20 include viscosity or polymerization data from the viscosity sensors 18, injection pressure data (such as injection force) from the injection pressure sensors 90 and intravertebral pressure data from the intravertebral pressure sensors 14. The signals from the sensors 14, 18, 90 can be amplified and digitized if required, for example if the sensors 14, 18, 90 generate relatively weak analog output signals.

The inputs received by the control module 20 further include a home position signal from the home position switch 104, as well as various control signals coming from the control panel 24, generated when the physician uses the command buttons, switches, knobs, etc. of the control panel 24. In a particular embodiment, the control signals are digital signals. The physician thus controls the injection process directly using the control panel 24. In a particular embodiment, the control signals from the control panel 24 include, for example, the desired cement delivery speed and volume, and commands to turn the system on, open the system to insert a syringe body, ready the plunger and syringe body for cement injection, inject the cement, reset for a different syringe body, reverse flow direction during the cement delivery, aspirate the bone marrow at a given speed, etc.

The outputs of the control module 20 include one or more actuation signals to control the driving system 62. In a particular embodiment, the actuation signals include a first signal starting/stopping the driving system 62, a second signal directing the driving system 62 to turn or translate in one of two opposed directions (e.g. clockwise or counter-clockwise rotation) so that the physician can use the system to both fill and empty the syringe body 58, and a third signal providing the speed of the movement of the plunger (e.g. signal in the form of a pulse instructing the driving system 62 to move one step, the control module 20 controlling the speed and number of steps, and as such the displacement of the plunger 60, through the number and rate of the pulses). In a particular embodiment, a driver (not shown) is interposed between the control module 20 and the driving system 62 in order to implement the actuation signal(s). The driver can be in the form of hardware or alternately be programmed in the microprocessor of the circuit board providing for the control module 20.

The other outputs of the control module 20 include the data to be displayed on the display unit 22 as mentioned above (e.g. viscosity, pressures, cement delivery rate or speed, total injected volume), as well as actuation signals to the micro-motor of the screw delivery mechanism 43 and/or to the vacuum system of the cannula 12a,b,c, if required.

In use and in a particular embodiment, the physician gives a command to open the device so that a syringe body can be inserted therein, for example by pressing a corresponding button on the control panel 24 to produce a corresponding control signal, preferably at the point of time of cement mixing. This causes the control module 20 to command the driving system 62 with the corresponding actuation signal(s) to move the syringe plunger 60 backwards until the home position switch 104 is activated, emitting the home position signal. Upon reception of the home position signal, the control module 20 stops the driving system 62 with the appropriate actuation signal(s), and the physician inserts the new syringe body 58. In this example the syringe body 58 is inserted in the delivery device already filled with cement, however as mentioned above the syringe body can alternately be inserted when empty and the system can be used to fill the syringe body with cement prior to injection.

When the syringe body 58 is inserted in the cement delivery device 16, the physician gives a second command to move the plunger 60 to an initial position for injection, for example by pressing a corresponding button on the control panel 24 to produce a corresponding control signal. This would typically occur soon (e.g. approximately one minute or less) after mixing of the cement. Upon reception of the control signal corresponding to the second command, the control module 20 instructs the driving system 62 to move the plunger 60 forward, for example step by step, with the corresponding actuation signal(s), until the injection pressure sensor 90 provides injection force data indicating that the plunger 60 is beginning to inject the cement from the syringe body 58. The control module 20 reads the data coming from the injection pressure sensor 90 and the other sensors 14, 18. Upon reception of the adequate injection force data, the driving system 62 is stopped by the control module 20 with the adequate actuation signal(s), and the control module 20 starts to continually send information to display on the display unit 22 and/or a computer.

After the plunger 60 is in position, the physician gives a third command to inject the cement, for example by pressing a corresponding button on the control panel 24 to produce a corresponding control signal. The physician typically gives this third command when the display unit 22 shows that the cement viscosity is appropriate. The control module 20 reads the data from the sensors 14, 18, 90, and calculates the needed injection force and the corresponding parameters (e.g. torque, speed) of the driving system 62. The control module 20 then activates the driving system 62, and as such the cement injection, through use of the corresponding actuation signal(s), in order to move the plunger 60 in a displacement-controlled, continuous manner. As well, at the same time, the control module 20 sends all the necessary information, including the data from the sensors 14, 18, 90, to the display unit 22 and/or computer. In a particular embodiment, the control module 20 only moves the driving system 62 as long as the physician gives the corresponding injection command, for example by holding a button depressed in the control panel 24, and if the command is broken (e.g. button released), the control module 20 stops the driving system 62 with the appropriate actuation signal(s) so that the injection is halted.

In a particular embodiment, the control module 20 provides pressure pulsations on the cement during delivery through actuating the driving system 62 in a pulsed manner. Pulsation enhances cement flow, and reduces the delivery pressure. An adequate mode of pulsation changes as the cement polymerizes. The pulsation mode will likely depend on the cement, and can be determined using a rheometer.

The cement delivery device 16 can also deliver haptic feedback of the intravertebral pressure to the physician. The control module 20 in this case gathers intravertebral signals, magnifies them, and sends a feedback signal to generate a contact force on the physician's hand during cement delivery, for example through a portion of the control panel 24. This feedback can be integrated in all designs.

Global Design

The cement delivery device 16 can be presented in a plurality of various exterior designs to achieve the present invention, any one of which can include and enclose any one of the mechanisms shown in FIGS. 8-10, a combination thereof, or any other appropriate mechanism transmitting power from the driving 62 to the syringe plunger 60.

Figure 20:
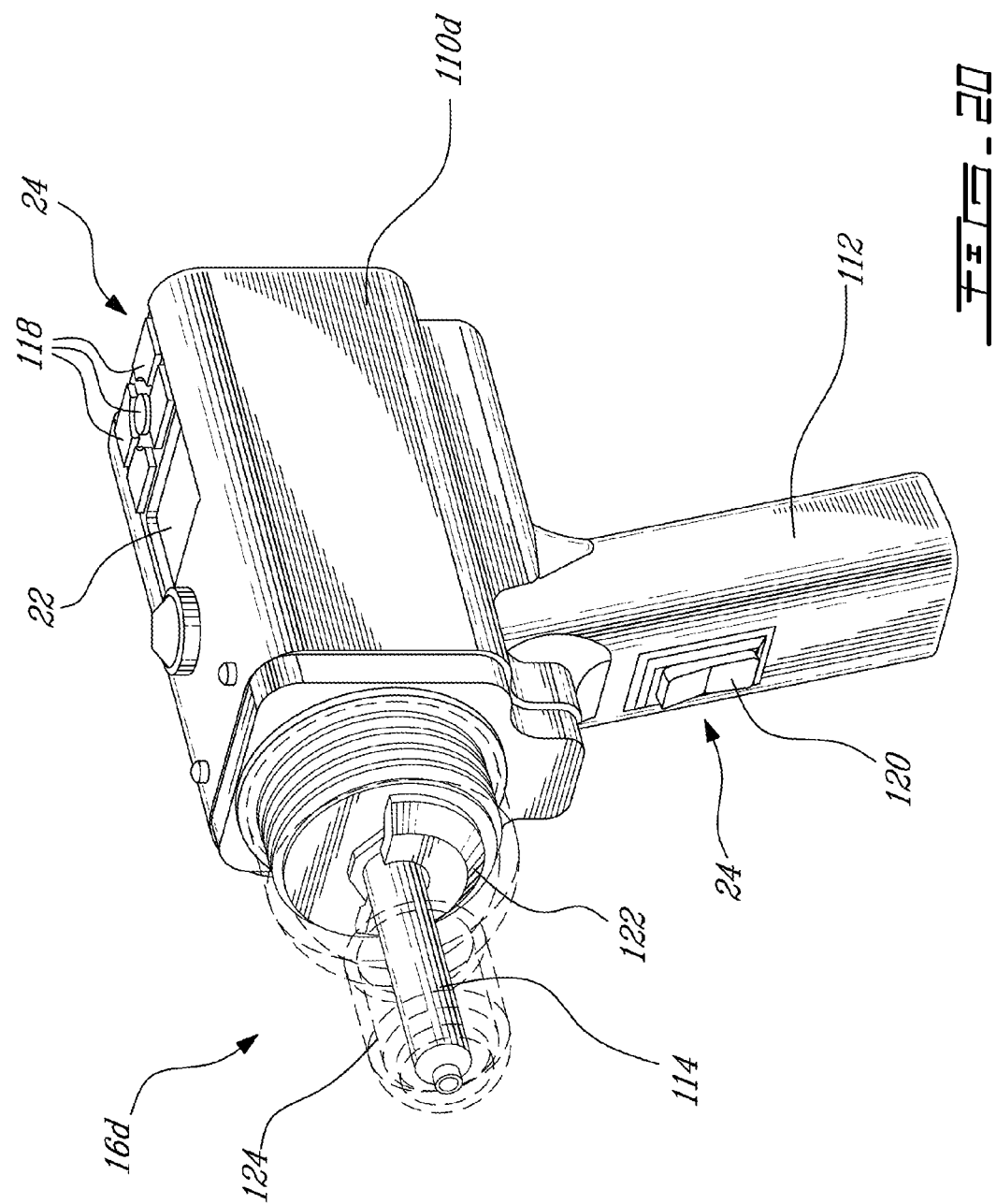
FIG. 20 is a tridimensional view of a cement delivery device according to a particular embodiment of the present invention.

FIG. 20 illustrates a particular embodiment 16d of the cement delivery device 16, which is in the shape of a cement gun and is simple and portable. The device 16d comprises three principle parts: a body 110d, a handle 112, and a syringe 114. The body 110d includes on a top face thereof the display unit 22, for example in the form of a LCD display screen, and command buttons 118 forming part of the control panel 24 to ensure easy access and utilization, the command buttons 118 allowing the physician to generate the control signals described above and shown in FIG. 19. The device 16d is operated by the handle 112, which is solidly attached to the body 110d. The handle 112 includes a command button 120 on the front thereof to control the cement injection, forming a second part of the control panel 24. In a particular embodiment, the command button 120 allows the physician to give the third or injection command described above.

Once the syringe 114 is filled with cement, it is positioned in a cylindrical cavity defined in a block 122 which is part of the body 110d. The device 16d also includes a translucent syringe support 124 that is screwed into the block 122. This stabilized the syringe 114 and eases the injection.

Figure 21:
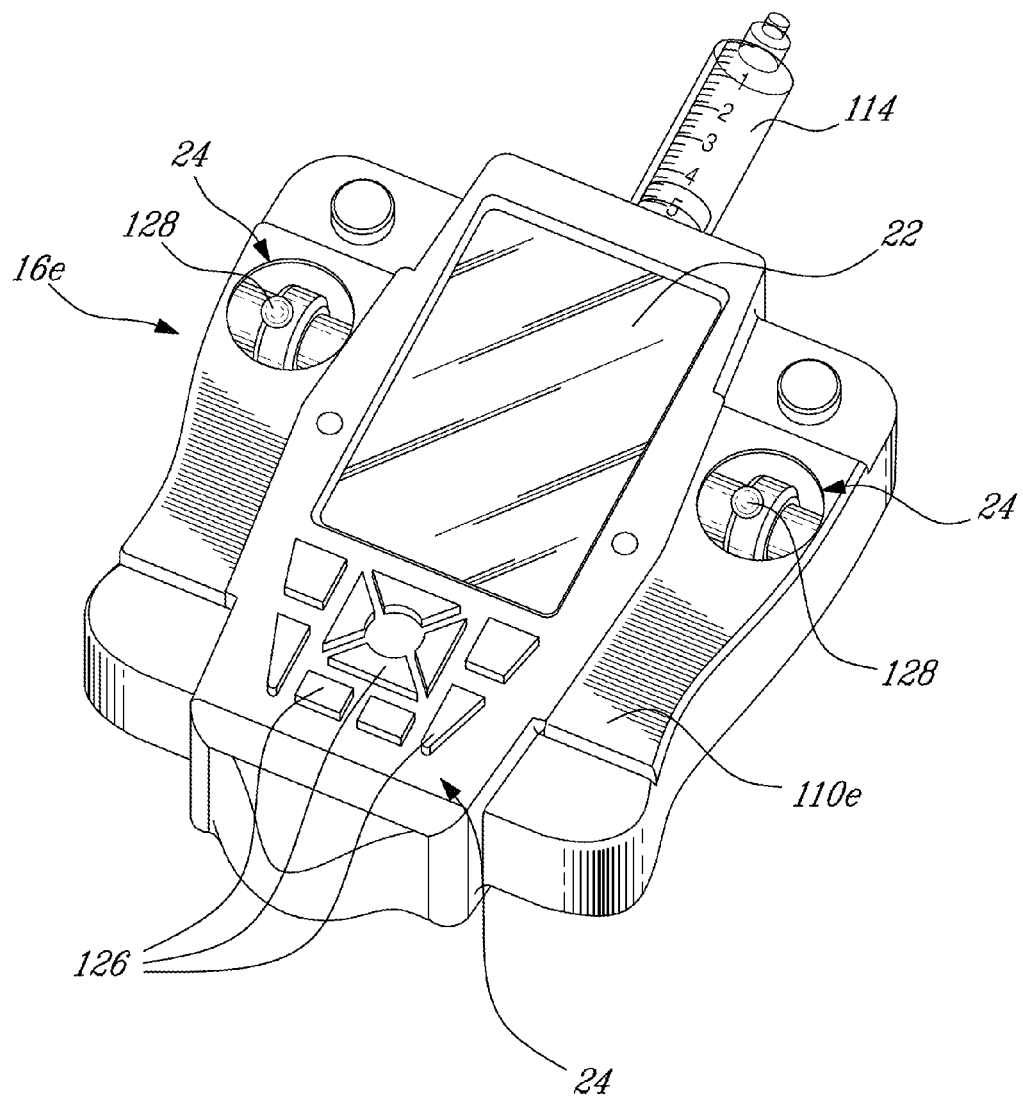
FIG. 21 is a tridimensional view of a cement delivery device according to an alternate embodiment of the present invention.

FIG. 21 illustrates another particular embodiment 16e of the cement delivery device 16, which is a portable apparatus comprising two principle parts: a body 110c and a syringe 114. The body 110e provides an easy to use and consistent interface, including the display unit 22, for example in the form of a large LCD display, and command buttons 126 defining part of the control panel 24 and located directly underneath the display unit 22 for easy access. In a particular embodiment, the command buttons 126 allow the physician to generate some of the control signals described above and shown in FIG. 19. The body 110e also includes two flexible levers 128 placed on opposite sides of the display unit 22 and forming another part of the control panel 24, to allow the physician to provide others of the control signals described above, such as for example the desired injection volume and speed of the cement. The body 110e is curved on both sides to allow for comfortable hand control of the levers 128.

Figure 22:
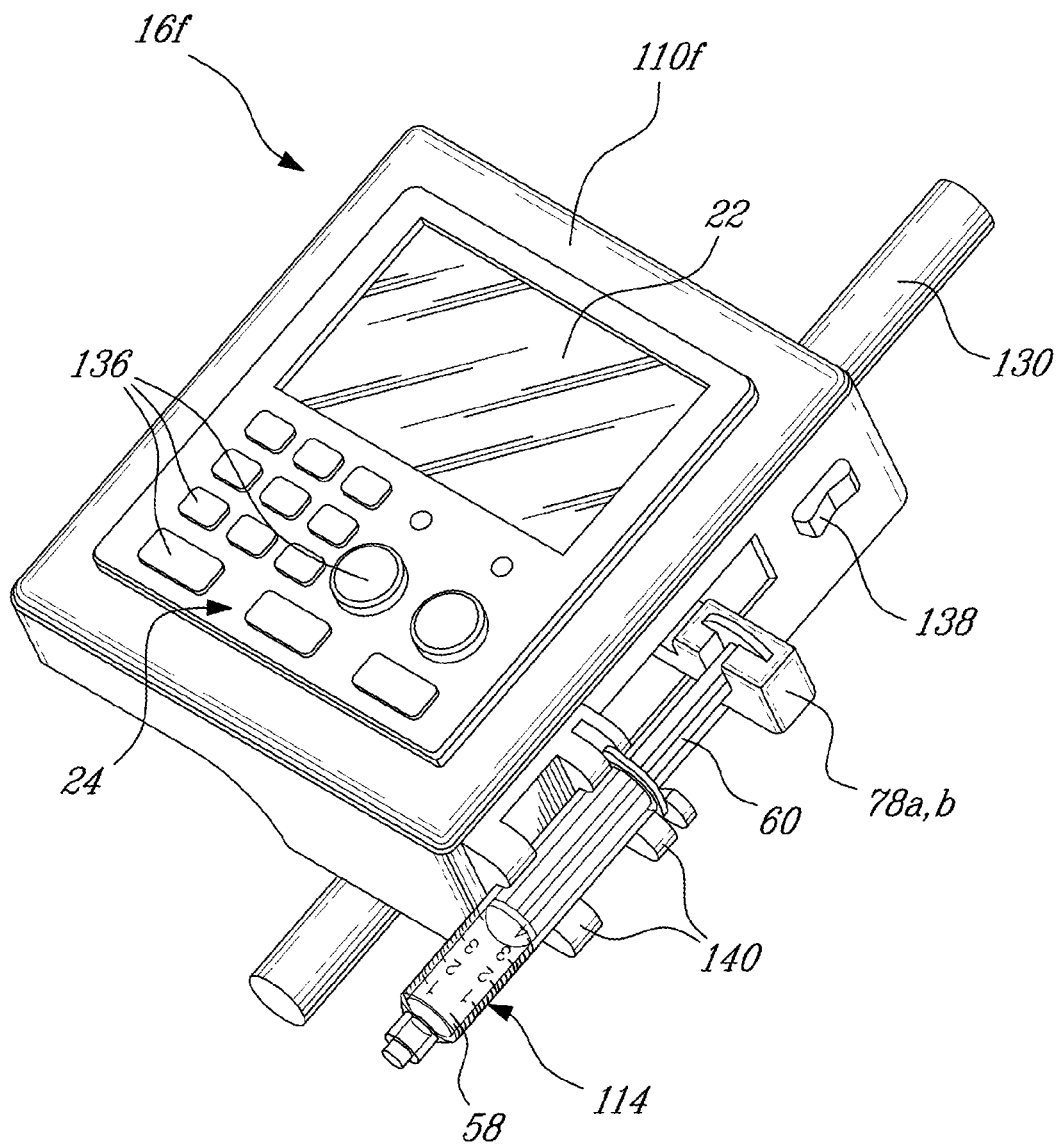
FIG. 22 is a tridimensional view of a cement delivery device according to an alternate embodiment of the present invention.

FIG. 22 illustrates another particular embodiment 16f of the cement delivery device 16, which is also simple and easy to use. The device 16f is vertically attached to a fixing bar 130, for example by surrounding fastener tightened by a screw, allowing the position of the device 16f to be easily adjusted on the bar 130.

The device 16f comprises three principle parts: a body 110f, the fixing bar 130, and a syringe 114. The body 110f includes on a side thereof a syringe support 140 that secures the syringe 114 once it is filled with cement. A pushrod such as shown for example at 78a,b in FIGS. 8-9 protrudes from the body 110f and engages the plunger 60 of the syringe 114, such that the movement to the pushrod 78a,b activates the plunger 60 which moves inside the syringe body 58 to force the injection of the cement.

The device 16f includes the display unit 22 on a front face of the body 110f, for example in the form of a large LCD display, thus improving visibility and access to the results. The control panel 24 is in the form of command buttons 136 placed underneath the display unit 22 where they are easily accessible. In a particular embodiment, the command buttons 136 allow the physician to generate the control signals described above and shown in FIG. 19. The body 110f further includes, on a side thereof, a button 138 to control a light.

Figure 23:
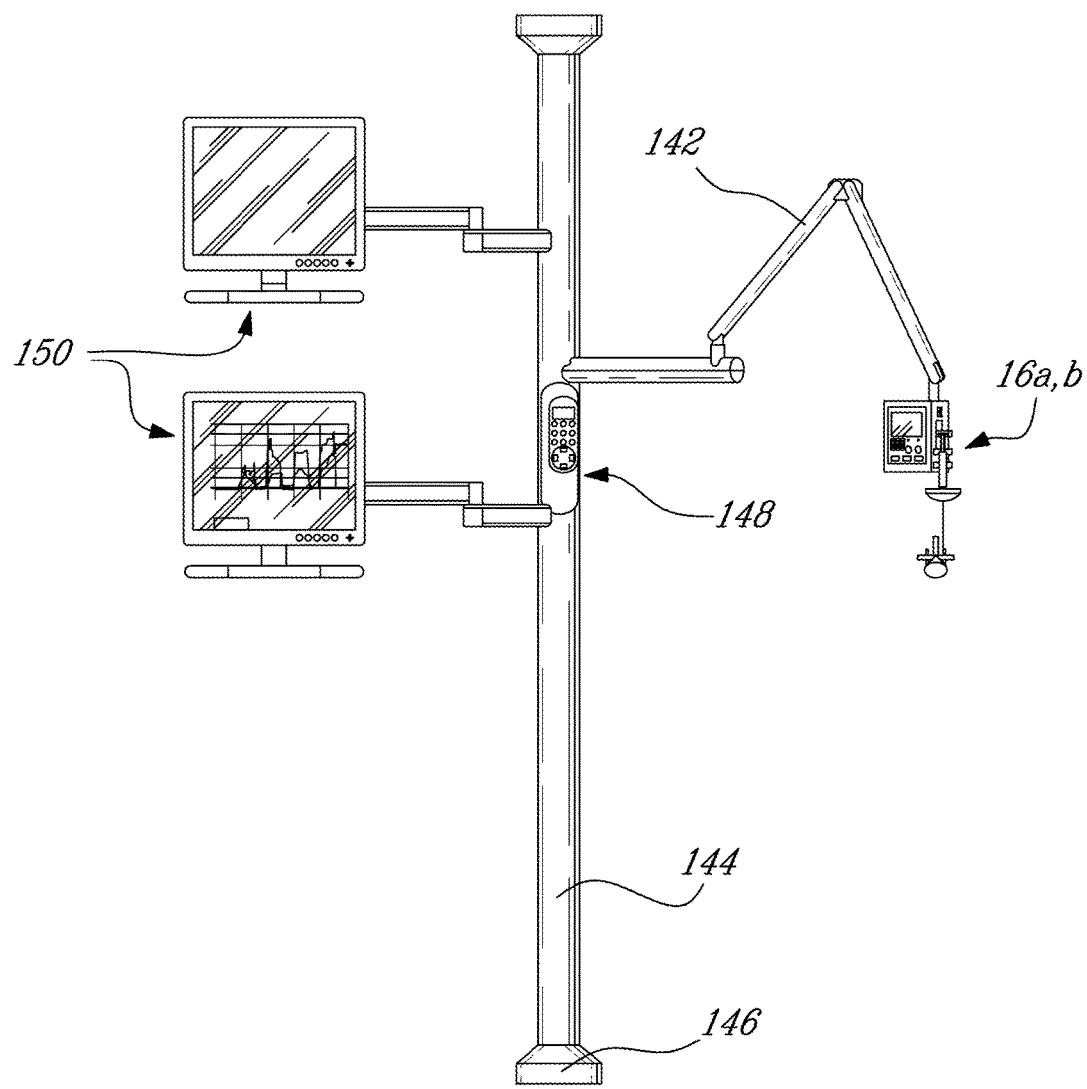
FIG. 23 is a tridimensional view of a cement delivery system according to a particular embodiment of the present invention, shown here in combination with the cement delivery device depicted in FIG. 22.

FIG. 23 shows a design for the cement delivery system 10 according to a particular embodiment which allows reduced x-rays exposure for the physician. The device 16f of FIG. 22 is shown supported by a flexible arm 142 which is attached to an upright post 144 extending from a base 146. Also supported on the post in an auxiliary control panel 148 allowing remote control of the position of the arm 142 and/or the same controls/commands provided by the control panel 24. Further supported on the post are auxiliary display units 150 providing a larger, easier to read display for the information displayed on the display unit 22 and/or any additional pertinent information, such as fluoroscopic visualization data. It is understood that the configuration of FIG. 23 can alternately be used with any other appropriate design for the cement delivery device 16.

The elements of the cement delivery device 10 thus help improve bone cement injection procedures, such as vertebroplasty. The displacement controlled cement delivery device 16a,b,c advantageously provides for a continuous, slow and precise cement delivery, with an injection pressure exceeding pressures that can be manually applied, thus allowing for thicker cement to be delivered. The viscosity sensors 18 provide for real time, in-situ monitoring of the cement curing, within the syringe body 58, thus allowing for the cement to be injected at its optimum viscosity. The cannulae 12a,b,c allow for bone marrow aspiration simultaneously with bone cement injection, which guides the bone cement within the bone as well as reduces the risks of emboli. The cannulae 12a,b,c with an intervertebral or other inner bone pressure sensor 14, either connected to a cannula conduit or embedded in the cannula itself, allow for monitoring of the intravertebral pressure, to ensure that there is no excess pressure within the bone, as well as for providing an indication that cement leakage is about to occur or is starting when a sudden drop of pressure is detected. The syringe equipped with a pressure sensor 90 allows for the determination of the injection pressure, which provides information on the pressure drop within the cannula and as such on the viscosity of the bone cement. Any one of these elements can be integrated in a typical cement delivery system, or alternately be combined with any one, any group of, or all of the others.

In a particular embodiment, the cement delivery system 10 is an integrated cement delivery system and includes the displacement-controlled cement delivery device 16a,b,c, the pressure sensors 14 and/or 90, the viscosity sensors 18, and the control system 102 including the control module 20, the display unit 22 and the control panel 24. This integrated system advantageously improves the safety and predictability of cement delivery, by providing warnings when the pressure is out of normal ranges, controlling the delivery of bone cement, and insuring that the cement has an appropriate viscosity on delivery to minimize the risk of leakage.

The cement delivery system 10 of the present invention allows the physician to control cement delivery by deciding on the injection rate and mode, total injection volume, and period of cement delivery. If required, the physician can adjust and overwrite the settings of the system 10.

The rod 70c is detachably connected to the head 88 or piston in the syringe. As the rod 70c advances it moves the piston against the cement. If for some reason the physician wishes to reduce the pressure applied to the cement he/she may press the button to stop the advance of the rod 70c. At the same time the direction of the movement of the rod may be reversed, for example approximately 0.1 mm in order to reduce the pressure on the cement. Since the rod is attached to the piston, it will be moved backwards as well. This way the same delivery mechanism can be used for depressurization.

The cement delivery system 10 described herein provides the advantage of concomitantly overcoming the limitation of excessive pressure and providing assistance to enhancing filling uniformity such as to reduce the risk of cement leakage. Additionally, the cost effective system 10 can be simply incorporated into the vertebroplasty procedure without substantially affecting or changing how the procedure is performed. Another advantage is that it provides physicians with real time monitoring of the cement delivery process, which is vital to guiding the intravertebral flow and preventing leakage, instead of reacting to visual fluoroscopic clues once leakage has occurred. Thus, the cement delivery system 10 allows the physician to prevent, or at least reduce the risk of, leakage rather than detecting it.

The system 10 also allows the guiding of the intravertebral cement filling during cement delivery, for example with the cannulae 12a,b,c, thereby enhancing filling uniformity and reducing leakage risk. Flow guidance is also improved by delivering cement of adequate viscosity. The miniature viscosity sensors 18 provide constant readings of polymerizing cement viscosity such as to inject cement having an optimal viscosity.

The system 10 ensures slow and continuous cement delivery, thereby leading to low intravertebral pressure and enhancing smoothness and precision of delivery. Accurate cement delivery and low pressure reduces leakage risk. More explicitly, precise delivery ensures exact filling volume, thereby reducing undesired excess cement which increases leakage risk. Continuous delivery results in steady flow, thereby reducing undesired transient peaks in pressure which augment leakage risk. Displacement-controlled delivery leads to stable cement flow conditions, thereby reducing the risk of sudden uncontrolled flow, which is difficult to monitor under fluoroscopy. Delivery forces of at least 2 KN reduce the risk of insufficient filling when delivering thick cement. With live monitoring of pressures and viscosity during procedures, physicians are alerted by acoustic or visual signals when polymerizing cement attains adequate viscosity of safe delivery. With this strengthening tool, physicians are alerted when delivery results in high unsafe pressures. Finally, with slow cement delivery, the physician has sufficient time to monitor intravertebral filling and if necessary to intervene, thereby preventing further leakage. The extended time of monitoring and reaction combined with fluoroscopic visualization enhance procedural safety.

The system 10, through the designs shown for the devices 16d,e,f, is ergonomically designed. The cement delivery device 16 is light and in a particular embodiment weighs approximately 0.5 kg. Physicians interact with it in a simple manner. The system 10 is also economical in design, with the main components being reusable. Disposable items are specialized syringes and cannulae, which can be bundled in a set.

The system 10 resulted from a thorough biomechanical understanding of the cement delivery process and forces governing the intravertebral flow in vertebroplasty. The system 10 and currently used fluoroscopic visualization can advantageously complete each other by attacking the problem from two different, yet, complimentary angles, the system 10 allowing a substantial reduction in the risk of leakage while the fluoroscopic visualization allowing the detection of leakage if leakage does occur. Thus, when combined together the two methods can provide a safer and more reliable vertebroplasty procedure, assisting the physician in foreseeing and preventing cement leakage.

In another embodiment, the cannula may be provided with a collar on the exterior wall to serve as a stopper which would limit the penetration of the cannula in the pedicle. In a particular embodiment, the collar is a simple annular ring surrounding the exterior wall, spaced apart from the proximal end.

Figure 24:
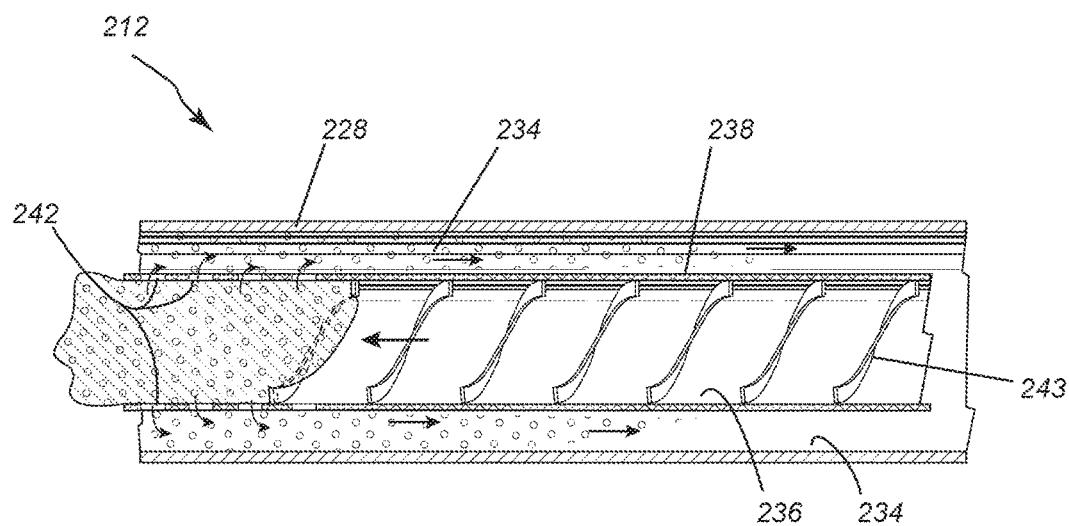
FIGS. 24-27 are fragmentary, schematic cross-sectional views of multi-lumen cannulae, according to various alternate embodiments.

The following description relates to the percutaneous cannulae 12a,b,c described herein. Referring now to FIG. 24, a multi-lumen cannula 212 includes an outer tubular wall 228 and a concentric inner tubular wall 238 defining an annular, peripheral passage 234 therebetween. A central conduit or passage 236 is delimited by the inner wall 238. A percutaneous delivery conveyor is provided in the central passage 236. In the embodiment shown, the delivery conveyor is a shaftless helical delivery screw 243, for example as described in U.S. Pat. No. 5,092,453 issued Mar. 3, 1992 to Bruke and incorporated herein by reference. The helical screw 243 includes a continuous helical blade with a helical edge proximate one of the tubular walls. In the embodiment shown in FIG. 24, a thick, flowable material can be moved towards a distal end of the central passage 236 by means of the helical delivery screw 243. The delivery screw 243 is spaced inwardly relative to the distal end of the tubular wall to which the helical edge of the blade is proximate. The thick flowable material may be a paste or it may be granular. The thick flowable material, for example a mineral-paste, is compressed by the helical delivery screw 243 forcing the liquid in the thick flowable material to seep through openings 242 defined in the wall 238 between the distal end of the wall and the end of the delivery screw. An aspirator or vacuum pump (not shown) communicates with the proximal end of the peripheral passage 234 in order to aspirate the liquid seeping into the peripheral passage 234. Tissue fluid may also circulate through the openings 242.

Figure 25:
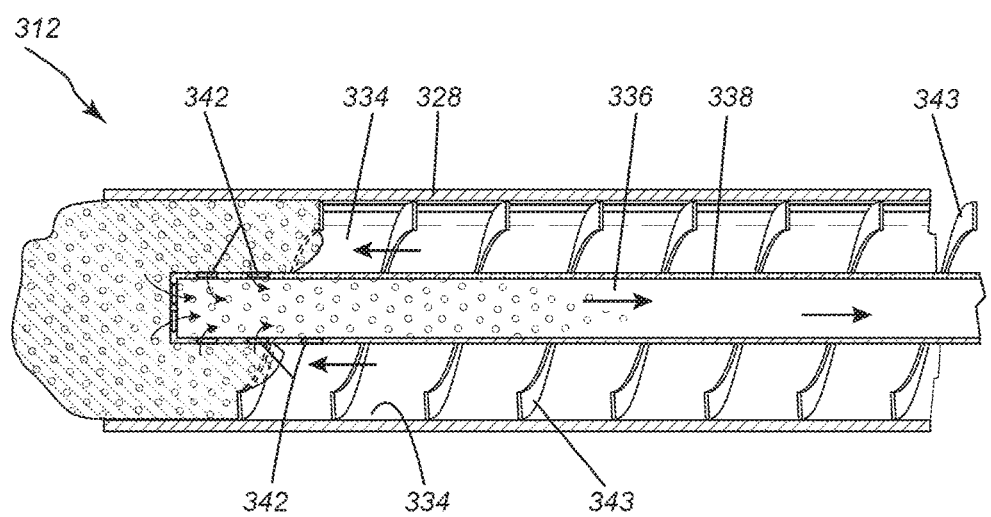

In the embodiment shown in FIG. 25, the multi-lumen cannula 312 includes an outer tubular wall 328 and a concentric inner tubular wall 338 forming a central conduit or passage 336 and a peripheral, annular conduit or passage 334. The delivery conveyor, for example a shaftless helical delivery screw 343 similar to that of the embodiment of FIG. 24, is provided in the peripheral passage 334 between the walls 328 and 338. Openings 342 are provided at the distal end region of the cannula in the inner wall 338. Thus, as the shaftless helical delivery screw 343 is rotated, the thick flowable (e.g. pasty) material advances towards the distal end where it is compacted, causing the liquid in the thick flowable material to seep through the openings 342 into the central passage 336. When delivering polymeric, viscous thick material where the compaction does not expel or segregate a liquid from the viscous material, for example medical cements, the inner wall 338 forming the central conduit 336 extends beyond the peripheral conduit 334 to allow aspiration of displaced bone marrow or other body fluids, as well as to guide the filling of the thick flowable material, during the delivery process. This assembly is useful to extract bone marrow, treat a lesion or fill the bone for example with PMMA cementitious material.

Figure 26:
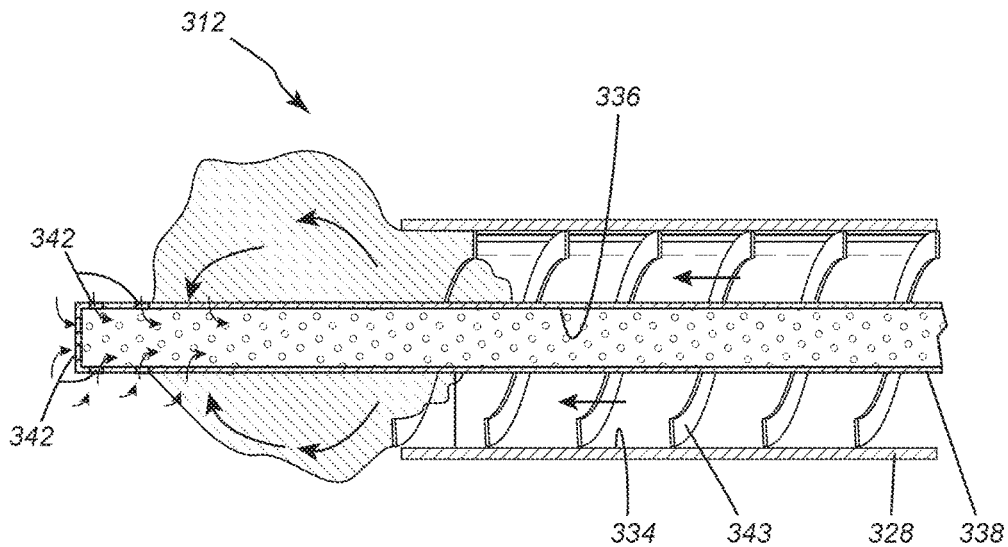

FIG. 26 illustrates an embodiment similar to that of FIG. 25, but in this case the inner tubular wall 338 extends beyond the distal end of the outer tubular wall 328. The openings 342 through the inner wall 338 are defined in the portion of the inner wall 338 that extends beyond the distal end of the outer wall 328.

Figure 27:
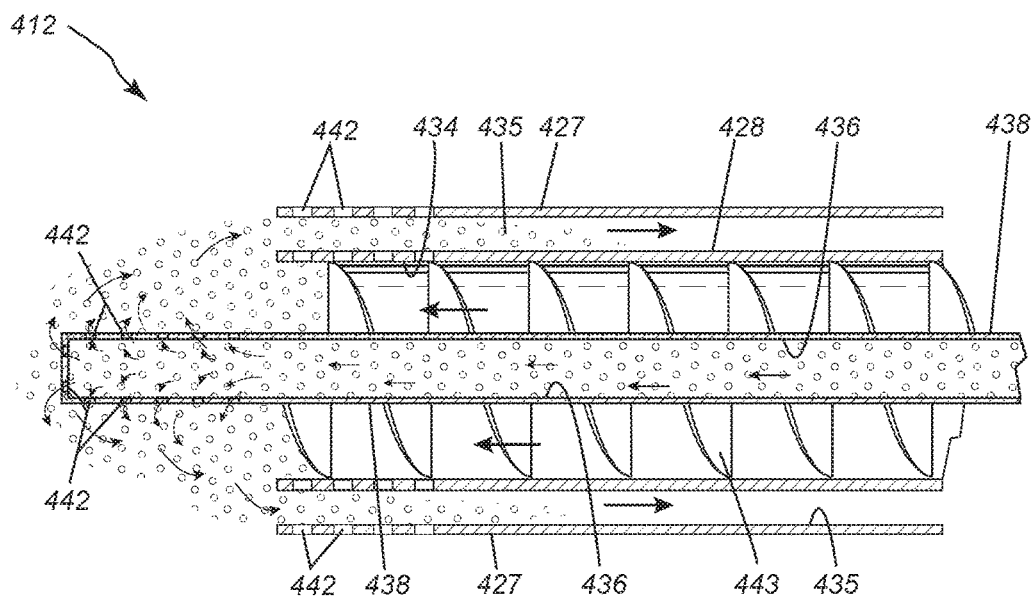

FIG. 27 shows a further embodiment of a multi-lumen cannula 412, including an inner tubular wall 438 surrounded by a concentric, intermediate tubular wall 428, which is surrounded by an outer tubular wall 427. A central passage 436 is defined by the inner wall 438, an intermediate passage 434 is defined between the inner and intermediate walls 438 and 428, and an outer passage 435 is defined between the intermediate and outer walls 428 and 427. A helical delivery screw 443 is fixedly mounted to outer surface of the inner wall 438 and rotates within the intermediate passage 434. The delivery screw 443 advances the thick flowable material, as previously discussed, while the central passage 436 is provided for the introduction of rinsing fluid. The rinsing fluid, as will be discussed, is meant to wash the area to be treated, while being drawn through the outer passage 435 by suction applied in this passage from the proximal end. Rinsing fluid as well as blood and other tissue and debris are drawn out by the suction applied to the outer passage 435. The outer wall 427 has openings 442 defined therethrough for passing the fluids drawn by the suction into the outer passage 435, for the purpose of drainage. Alternatively, the rinsing fluid may be introduced through the outer passage 435 and withdrawn through the central passage 436. Further, the thick flowable material can be introduced using the delivery screw 443 and both the outer and central passages 435 and 436 can be used to extract the bone marrow.

In a particular embodiment, the rinsing fluid is a saline solution heated above 37° C. The rinsing fluid may contain a therapeutic medication for the bone, a palliative medication for the bone and/or a radio-opaque material.

Alternately, the cannula may include a single lumen receiving the shaftless delivery screw 243, for example, the cannula 212 of FIG. 24 where the outer wall 228 is omitted. Such a cannula may be used to deliver a viscous material, granular material and/or rinsing fluid similarly to the cannulae 212, 312, 412. A central tube may optionally be inserted within the central opening defined in the screw 243, for example for aspiration.

The bone can thus be treated by delivering a viscous material into cancellous bone through one of the passages of the multi-lumen cannulae 212, 312, 412, and leaving another one of the passages of the cannula open to drain the rinsing fluid (if used) or other fluids when displaced by the viscous material. The viscous material (and rinsing fluid if used) are injected into the bone through the proximal inlet port communicating with the passage used for injection, and the proximal inlet port of passage used for draining is used for rinsing or aspiration.

As discussed above, the cannulae 212, 312, 412 of FIGS. 24-27 (as well as the single lumen embodiment with delivery screw) are particularly suitable for use with thick flowable material. In the present specification and claims, the term "thick flowable material" refers to a material which is isotropic and has the viscoplastic behavior of the generalized Herschel-Bulkley fluid model, wherein the material behaves as a solid body while it is below its critical shear stress. Once the critical shear stress (or "yield stress") is exceeded, the material flows like a viscoplastic fluid. The term "solid body" implies that the material does not flow readily unless the yield stress is exceeded. Wax, butter, and petroleum jelly are examples of such flow behavior and a material having a flow behavior similar to these materials may be used.

In the case of a percutaneous intervention with a cannula, a syringe or reservoir is filled with a plug of thick flowable material, and then pressure is applied to the plug using a plunger until the applied pressure exceeds the yield stress characteristic of the material, at which time it will behave like a fluid and thus becomes flowable, to the point of being extruded through the cannula. Yet, once the material exits the distal end of the cannula, the extruded material behaves as a solid body and becomes immobile and thick. The advantage is that this class of material has a much reduced risk of leakage when injected into a bone cavity or other body tissue cavity.

In a particular embodiment, the yield stress of the thick flowable material is at least 100 kPa in order to avoid becoming fluid-like and mobile under the effect of blood pressure. An estimated yield stress of 1 MPa is below the yield stress of the cancellous bone tissue, thus the thick flowable material may be extruded into the cancellous bone bed without destroying the cancellous bone structure. It is known that the yield stress of the cancellous bone is not fixed, as it varies with osteoporotic conditions. The yield stress of the osteoporotic cancellous bone is estimated to be in the range of 1 MPa. Accordingly, in a particular embodiment, the yield stress of the thick flowable material is at least 100 kPa and well below 1 MPa, so as to avoid damage the osteoporotic cancellous bone. For example, the yield stress is lower than the yield stress of the cancellous bone by at least 0.5 MPa to reduce the risk of damage. Furthermore, thick flowable materials with higher yield stress characteristics require higher injection or extrusion forces to be applied to the reservoir. The extrusion forces are also related to the injection geometry and the thick flowable material's viscous behavior, which may vary depending on the tissue being treated.

Furthermore, viscoplastic fluid behavior causes the thick flowable material to flow as a viscous fluid, and to not have memory. Also of interest, is that the thick flowable material, once it enters the viscoplastic flow condition, has a high level of extensibility and/or deformation without fracturing or disintegrating. For example, in a particular embodiment, the thick flowable material has a level of extensibility allowing the material to be stretched up to 3 times its original length without fracturing or disintegration. This is advantageous since a material that fractures, disintegrates, fragments or breaks when deformed leaks easily. A thick flowable material that can be stretched and exhibits under tensile test a large deformation up to several hundred percent compared to its original length does not leak easily. In a particular embodiment, the thick flowable material selected has the elongation behavior of a fluid, behaves viscoplastically, and has no significant memory. In rheology sciences, the term 'extensional or elongation viscosity' is often used to describe such elongation behavior. A typical example of a desired thick flowable material properties are that of chewing gum. Chewing or bubble gum may, for example, be blown into a bubble or stretched as a film, uniformly without fragmenting of fracturing. The gummy like material is often characterized, among others, as having a storage modulus higher than 0.1 MPa, when measured at room temperature using a rheometer oscillating at 5 Hz. A Deborah number used to describe the flow properties of chewing and bubble gum is in the range of from 0.5 to 5.

PMMA paste, as it hardens due to the dissolution and polymerization, may temporarily become dough-like. The state of the art thus far focused on the viscosity of the PMMA paste, assuming that it is the viscosity that renders the PMMA paste cohesive and that the viscous paste provided a reduced risk of leakage. The inventor has found that it is instead the gummy-like, extensibility behavior and the yield stress of the material that provides its cohesive behavior. The cohesiveness of a material is related to its extensibility behavior. In bone augmentation procedures, it has been observed that leakage results mainly because of damage in the bone structure or of blood vessels, forming a region of least resistance, and that the cement paste follows this path of least resistance to the flow. This leakage can be reduced by ensuring that the PMMA paste has the properties of a thick flowable material as described above.

The cannulae 212, 312, 412 of FIGS. 24-27 (as well as the single lumen embodiment with delivery screw) may also be used to percutaneously deliver materials such as polymeric or mineral pastes (e.g. calcium phosphate paste), powders, granules, pellets or capsules. The delivery screw 243, 343, 443 can transport almost any class of material. Another advantage of the delivery screw 243, 343, 443 is that it is flexible and can be bent to a curve. As such, the delivery screw 243, 343, 443 can function in a curved tube or catheter. The conveyor formed by the delivery screw 243, 343, 443 including tubes 228, 328, 238, 338, etc., can be made from flexible or rigid materials, and may be curved. The conveyor can be fabricated by machining, extrusion or molding. The delivery screw 243, 343, 443 can also be used as a feeder to fill the material into an elongated catheter, and a stylet can be then used to push the material from within the catheter into a body region. The assemblies shown in FIGS. 24 to 27 have a proximal inlet port communicating with each passage (not shown), where the thick flowable material may be loaded into the selected delivery passage. As mentioned above, when the feature of aspirating body tissue or fluid is not required, the delivery screw 243 can be placed within a single lumen cannula, to deliver biomaterials, for both diagnostic and therapeutic purposes, into the body tissue. As such, the delivery screw 243 may be useful for delivering biomaterials into body tissue affected by soft tissue, cystic or liquefied lesions including but not limited to myelomas. The delivery screw 243, 343, 442 is sized and configured to be introduced into a cannula. The cannula is sized and configured for percutaneous introduction into body tissue. In a particular embodiment, the delivery screw 243, 343, 442 has 2 to 5 pitches per centimeter.

For calcium-phosphate pastes that form cements, the compaction reduces the liquid content of the paste, therefore reducing the porosity thereof and accordingly increases the strength of the cement once hardened. In addition, starch grains or other fast-absorbing material grains can be added to the calcium-phosphate paste. Once hardened, the grains are gradually absorbed or dissolved; the cement then features an in-situ porous space, which is advantageous for the resorption of the calcium-phosphate cement and for the regeneration of the bone. The grain dimension can be as large as can be fit into the pitch distance of the delivery screw.

Another form of flowable materials which may be introduced percutaneously with the multiple-lumen cannulae 212, 312, 412 of FIGS. 24-27 is a granular or powder-like material. In a particular embodiment, the smallest grain size of granular material which may be used is about 1 µm, and the upper size limit is 6 mm; in a particular embodiment, the grain size is about 5 mm. The delivery screw 243, 343, 443 reduces the jamming or arching effect common to granular materials. The grains of the granular materials may be solid such as the grains of calcium phosphate used in bone repair or drug delivery. The grains may also be soft such as soft polymeric particles or capsules containing drugs. These materials can gradually dissolve to release medicinal, therapeutic and/or palliative agents. Another example of granulate material which may be used as a graft medium or repair material to facilitate the repair of bone defects is a finely chopped cortical or cancellous bone chips. The finely chopped bone chips can be delivered using the delivery screw mechanism. It can be augmented with other granular materials or bone morphogenetic proteins (BMP).

The space determined by the pitch of the threads make the transport of larger granules possible. Soft and hard granules can be used to help regenerate tissue, deliver medication, and/or to palliatively or therapeutically treat lesions. A percutaneous delivery cannula of 8 g has an internal diameter of 3.2 mm. Accordingly, granules of 3 mm and closer to the size and pitch of the 8 g cannula can be percutaneously delivered to the lesion. A proximal feeder can be used to feed the granules into the cannula harboring the delivery screw 243, 343, 443. Larger diameter cannulae can be used to deliver larger granules of up to 6 mm.

The method of harvesting bone marrow includes using a thick flowable material injected through one lumen and aspirating the bone marrow through a second lumen. The thick flowable material may be a medical gel, nano-structured cellulose-based gels or as identified above, for example a gummy-like material (medical gel or other).

Debridement of infected tissue from lesions to improve the healing potential of the remaining healthy tissue is a common medical procedure. A biocompatible material may be delivered into a cavity left by the lesion being displaced using one of the cannulae described above. In the case of an osseous lesion, once the lesion is removed, a load-bearing material (e.g. medical cement) is introduced in the lesion cavity for the purpose of augmenting the affected osseous structure. It is desirable to fill the lesion cavity with biomaterials or granules, preferably doped with medicine to help in the healing of the lesion and tissue surrounding it. This is referred to as a percutaneous grafting approach. For example, the injected biocompatible material may be a thick flowable material including a medical gel doped with therapeutic agents.

When removing a tumor, there may be some residue along the edges of the tumor that are too small to be detected, and if not removed, could cause a relapse. Therefore, it is desirable to fill the cavity after removing the lesion tissue with thick flowable biomaterials or granules to help destroy the tumor residue. These biomaterials may be strengthened with chemotherapeutic, lysing, ablating, palliative, therapeutic, and/or destructive agents. Hydro-thermal ablation is another technique to destroy lesions. The regional perfusion of hot liquid, which also can be augmented with therapeutic and other agents, may be introduced into the lesion from one lumen and aspiration may be applied through another lumen, as described above. A continuous hyper-thermic flow regime can be established to destroy the tumor using a single percutaneous access incision. Further, the localized and controlled flow of the heated water reduces the risk of the ablating water or fluid damaging other adjacent tissue. The ablating fluid may be radio-opaque. Alcohol ablation of bone and soft tissue lesion is also contemplated. This method is limited by the unpredictable flow of ethanol through the tumor and peritumoral tissues, particularly in cortical bone. Specifically, Ethanol necrotizes cells and indirectly leads to vascular thrombosis and ischemia. It is, therefore, desirable to control the flow of alcohol to ablate the lesion. Ethanol can be injected into the tumor directly using one passage of the cannula, and another passage of the multi-lumen cannula can used to aspirate the alcohol/ethanol, and therefore a continuous flow regime can be established. The cannula thus be used to introduce an ablative or destructive agent to treat a lesion in tissue (e.g. bone). In a particular embodiment, the ablative or destructive agent includes one of dehydrated alcohol, phenol, and radioactive material, and may be in the form of a thick flowable material.

A percutaneous procedure known as subchondroplasty is utilised to treat subchondral bone defects, due to bone marrow lesions, by the delivering bone-substitute material to the cancellous bone structure in order to gradually resorb and help regenerate the bone structure or to re-establish the vertical load-bearing capacity of the bone. Bone marrow lesions may relate to trauma, insufficiency injury, and aggressive pathologies such as infections or neoplastic conditions. A bone marrow lesion may not heal without treatment, making it a chronic insufficiency that may cause damage to the adjacent joint. Therefore, timely treatment helps reduce the risk of joint degeneration, and reduce the need to a joint replacement surgery. The multi-lumen cannula 212, 312, 412 is useful to prepare the bone affected by the lesion, including but not limited to rinsing, ablation and to receive the reinforcing and regenerating bone-substitute material. A similar procedure is the percutaneous management of peri-prosthetic osteolytic lesions around orthopaedic implants. These lesions are a cause of instability in the bone surrounding the implant which may lead to mechanical failure. Alternatively, it can be treated by the delivery of bone-substitute material doped with medication to the affected bone structure.

Inflatable devices such as osseous balloons are often used to form a cavity in internal body regions. These balloons are, for example, introduced percutaneously to form a cavity in the cancellous bone, to provide a region of least resistance for the purpose of receiving medical cement or other biocompatible thick material to be delivered to fill in the cavity. As such, the central conduit 236, 336, 436 of the multi-lumen cannula 212, 312, 412 may be used to introduce the balloon to form the cavity in the cancellous bone bed. The bone marrow and other tissue that is displaced when inflating the balloon is then aspirated through an outer lumen of the cannula by applying a negative pressure through the outer lumen, thus reducing the embolic load of the procedure. In addition, while the balloon is still inflated, the outer lumens can be used to rinse the cancellous bone bed around the balloon and to prepare the bone adjacent to the balloon in order to receive medical cement once the balloon has been retrieved.

It is understood that the any one of the multi-lumen cannulae 212, 312, 412 may be substituted for any other cannula described herein, for example for the percutaneous cannulae 12, 12a, 12b, 12c, and/or with any combination of the various elements described herein (e.g. cement delivery device, sensors, control system).

The above description is meant to be exemplary only, and one skilled in the art will recognize that changes may be made to the embodiments described without departing from the scope of the invention disclosed. Modifications which fall within the scope of the present invention will be apparent to those skilled in the art, in light of a review of this disclosure, and such modifications are intended to fall within the appended claims.

The invention claimed is:

1. A method of harvesting bone marrow, comprising:
percutaneously introducing a multi-lumen cannula into a cancellous bone;
applying suction through a first passage defined in a first lumen of the cannula;
injecting a thick flowable material into the bone from a second passage in a second lumen of the cannula;
extruding the thick flowable material through a distal end of the cannula into the cancellous bone in order to displace the bone marrow and other bone fluids, the suction applied through the first passage providing a hydraulic force guiding the displaced bone marrow; and
collecting the displaced bone marrow for a therapeutic or diagnostic purpose.

2. The method as defined in claim 1, wherein the thick flowable material is a biocompatible medical gel.

3. The method as defined in claim 1, wherein the thick flowable material is a biocompatible gummy-like material with high extensibility.

4. The method as defined in claim 3, wherein the gummy-like material has a storage modulus higher 0.1 MPa when measured at room temperature using a rheometer oscillating at 5 Hz.

5. The method as defined in claim 4, wherein the gummy-like material is a medical gel.

6. The method as defined in claim 1, wherein the thick flowable material has a flow behaviour similar to that of petroleum jelly.

7. The method of harvesting bone marrow as defined in claim 1, wherein the thick flowable material is in the form of granular material.

8. The method of harvesting bone marrow as defined in claim 3, wherein the thick flowable material has a yield stress above 100 kPa.

9. The method of harvesting bone marrow as defined in claim 1, wherein the thick flowable material has the following properties:
the material forms a solid body at room temperature while below a yield stress of the material;
the material is flowable when mechanical pressure causing a stress exceeding the yield stress is applied thereon; and
the material becomes a solid body when the mechanical pressure is removed.

10. The method of harvesting bone marrow as defined in claim 9, wherein the material has a yield stress above 100 kPa.

11. The method of harvesting bone marrow as defined in claim 9, wherein the material is a medical gel having a level of extensibility allowing the thick flowable material to be stretched up to 3 times an original length thereof without fracturing or disintegration.

12. The method of harvesting bone marrow as defined in claim 9, wherein the material has a flow behaviour similar to that of petroleum jelly, or is a nano-structured cellulose gel.

13. The method of harvesting bone marrow as defined in claim 9, wherein the material is in the form of granular material.

14. The method of harvesting bone marrow as defined in claim 13, wherein a grain size of the granular material is at least 1 μm and at most is 6 mm.

* * * * *